(12) United States Patent
Mattsson et al.

(10) Patent No.: US 9,164,101 B2
(45) Date of Patent: Oct. 20, 2015

(54) ALLERGEN

(75) Inventors: Lars Mattsson, Uppsala (SE); Jonas Lidholm, Knivsta (SE); Thomas Lundgren, Uppsala (SE)

(73) Assignee: Phadia AB, Uppsala (SE)

( * ) Notice: Subject to any disclaimer, the term of this patent is extended or adjusted under 35 U.S.C. 154(b) by 0 days.

(21) Appl. No.: 13/642,259

(22) PCT Filed: Apr. 26, 2011

(86) PCT No.: PCT/SE2011/050503
§ 371 (c)(1),
(2), (4) Date: Oct. 19, 2012

(87) PCT Pub. No.: WO2011/133105
PCT Pub. Date: Oct. 27, 2011

(65) Prior Publication Data
US 2013/0045233 A1 Feb. 21, 2013

(30) Foreign Application Priority Data
Apr. 23, 2010 (SE) ...................................... 1050406

(51) Int. Cl.
*A61K 39/00* (2006.01)
*A61K 39/35* (2006.01)
*A61K 39/36* (2006.01)
*C07K 1/00* (2006.01)
*C07K 14/00* (2006.01)
*C07K 17/00* (2006.01)
*G01N 33/68* (2006.01)
*C07K 14/47* (2006.01)

(52) U.S. Cl.
CPC ............ *G01N 33/6854* (2013.01); *A61K 39/35* (2013.01); *C07K 14/47* (2013.01); *G01N 2800/24* (2013.01)

(58) Field of Classification Search
None
See application file for complete search history.

(56) References Cited

PUBLICATIONS

Felix et al. 'Allergens of horse dander: Comparison among breeds and individual animals by immunoblotting.' J. Allerg. Clin. Immunol. 98:169-171, 1996.*
Wade et al. "Genome sequence, comparative analysis, and population genetics of the domestic horse." Science 326:865-867, 2009.*
Larreta et al. 'Antigenic properties of the *Leishmania infantum* GRP94 and mapping of linear B-cell epitopes.' Immunology Letters 80: 199-205, 2002.*
Kim et al. 'Protein immobilization techniques for microfluidic assays.' Biomicrofluidics 7, 041501, 2013.*
Goel et al. http://www.rpi.edu/dept/chem-eng/Biotech-Environ/IM-MOB/goel2nd.html., 1994.*
Akdis, Cezmi., Allergy and Hypersensitivity Mechanisms of Allergic Disease, Current Opinion in Immunology, 2006, 18: pp. 718-726.
Akdis, Mubeccel and Akdis, Cezmi., Mechanisms of Allergen-Specific Immunotherapy, J. Allergy Clin Immunol, vol. 119, No. 4, Apr. 2007, pp. 780-789.
Breiteneder, K. et al., Recombinant Allergens; Basic and Practical Considerations, 8th International Paul Ehrlich Seminar, 1997, pp. 80-86.
Cabanas, R. et al., Importance of Albumin in Cross-Reactivity Among Cat, Dog and Horse Allergens, J Invest Allergol Clin Immunol, Mar.-Apr. 2000, vol. 10(2), pp. 71-77.
Cromwell, Oliver et al., Strategies for Recombinant Allergen Vaccines and Fruitful Results from First Clinical Studies, Immunology and Allergy Clinics of North America, 26 (2006), pp. 261-281.
Dandeu, J.-P. et al, Hydrophobic Interaction Chromatography for Isolation and Purification of Equ.c1, the Horse Major Allergen, Journal of Chromatography, 621 (1993), Elsevier Science Publishers B.V., pp. 23-31.
Demoly, P. et al., Allergy Review Series X: Progress in Diagnosis of Allergy in Vitro, Allergen-Induced Mediator Release Tests, Allergy 2003: 58: pp. 553-558.
Ebo, D.G. et al., In Vitro Allergy Diagnosis: Should We Follow the Flow?, Clinical and Experimental Allergy 2004; 34: pp. 332-339.
Goubran Botros, H. et al., Cross-Antigenicity of Horse Serum Albumin with Dog and Cat Albumins: Study of Three Short Peptides with Significant Inhibitory Activity Towards Specific Human IgE and IgG Antibodies, Immunology 1996, vol. 88, pp. 340-347.
Goubran Botros, H. et al., Thiophilic Adsorption Chromatography: Purification of Equ c2 and Equ c3, Two Horse Allergens from Horse Sweat, Journal of Chromatography B, vol. 710 (1998), pp. 57-65.
Goubran Botros, H. et al., Biochemical Characterization of Surfactant Properties of Horse Allergens, Eur. J. Biochem. 268, (2001), pp. 3126-3136.
Gregoire, C. et al., cDNA Cloning and Sequencing Reveal the Major Horse Allergen Equ c1 to be a Glycoprotein Member of the Lipocalin Superfamily, The Journal of Biological Chemistry, The American Society for Biochemistry and Molecular Biology, Inc., vol. 271, No. 51, Dec. 20, 1996, pp. 32951-32959.
Gronlund, H. et al., The Major Cat Allergen, Fel d 1, in Diagnosis and Therapy, International Archives of Allergy and Immunology, 2010; 151, pp. 265-274.
Hiller, R. et al., Microarrayed Allergen Molecules: Diagnostic Gatekeepers for Allergy Treatment, The FASEB Journal, vol. 16, Mar. 2002, pp. 414-416.
Jutel, M. et al., Allergen-Specific Immunotherapy with Recombinant Grass Pollen Allergens, J. Allergy Clin Immunol, vol. 116, No. 3, Sep. 2005, pp. 608-613.
Kim, J.L. et al., Current Asthma and Respiratory Symptoms Among Pupils in Relation to Dietary Factors and Allergens in the School Environment, Indoor Air 2005, 15: pp. 170-182.
Klug, J. et al., Uteroglobin/Clara Cell 10-kDa Family of Proteins: Nomenclature Committee Report, Annals New York Academy of Sciences, pp. 348-354.
Liccardi, G. et al., Sensitization to Horse Allergens in Italy: A Multicentre Study in Urban Atopic Subjects without Occupations Exposure, International Archives of Allergy and Immunology, 2011; 155, pp. 412-417.

(Continued)

*Primary Examiner* — Nora Rooney
(74) *Attorney, Agent, or Firm* — Porter Wright Morris & Arthur LLP

(57) ABSTRACT

An isolated horse allergen is disclosed which is a secretoglobin having a molecular weight of 15 kDa under non-reducing conditions and comprising a first peptide chain having a molecular weight of about 5 kDa and a second peptide chain having a molecular weight of about 10 kDa linked together, and variants and fragments thereof sharing epitopes for antibodies therewith. The use of the allergen in diagnosis and therapy is also disclosed as well as a diagnostic kit and a pharmaceutical composition containing the allergen.

5 Claims, 20 Drawing Sheets

(56) References Cited

PUBLICATIONS

Dewitt, A Marknell, et al., Molecular and Immunological Characterization of a Novel Timothy Grass (*Phleum pratense*) Pollen Allergen, Phl p. 11, Clinical and Experimental Allergy 2002; 32: pp. 1329-1340.

Mattsson, Lars et al., Prostatic Kallikrein: A New Major Dog Allergen, Journal of Allergy and Clinical Immunology, Feb. 2009, vol. 123, No. 2, pp. 362-368 and 368.e1-368.e3.

McDonald, Rhona E. et al., Latherin: A Surfactant Protein of Horse Sweat and Saliva, PLoS ONE, May 2009, vol. 4, Issue 5, e5726, pp. 1-12.

Ronmark, Eva et al, Different Sensitization Profile for Asthma, Rhinitis, and Eczema Among 7-8-Year Old Children: Report From the Obstructive Lung Disease in Northern Sweden Studies, Pediatric Allergy and Immunology 2003, 14: pp. 91-99.

Saarelainen, S. et al., Animal-Derived Lipocalin Allergens Exhibit Immunoglobulin E Cross-Reactivity, Clinical and Experimental Allergy 2007, 38, pp. 374-381.

Saarne, T. et al., Rational Design of Hypoallergens Applied to the Major Cat Allergen Fel d 1, Clinical and Experimental Allergy 2005, 35, pp. 657-663.

Smith, W. et al., Fel d 4, a Cat Lipocalin Allergen, Clinical and Experimental Allergy 2004, 34, pp. 1732-1738.

Spitzauer, S. et al., Characterisation of Dog Allergens by Means of Immunoblotting, Int Arch Allergy Immunol 1993, 100 pp. 60-67.

Stumvoll, S. et al., Identification of Cross-Reactive and Genuine *Parietaria judaica* Pollen Allergens, J. Allergy Clin Immunol, May 2003, vol. 111, No. 5, pp. 974-979.

Tutluoglu, B. et al., Sensitization to Horse Hair, Symptoms and Lung Function in Grooms, Clinical and Experimental Allergy 2002, 32, pp. 1170-1173.

Wainstein, BK et al., Combining Skin Prick, Immediate Skin Application and Specific-IgE Testing in the Diagnosis of Peanut Allergy in Children, Pediatric Allergy and Immunology 2007: 18: pp. 231-239.

Valenta, R. et al., The Recombinant Allergen-Based Concept of Component-Resolved Diagnostics and Immunotherapy (CRD and CRIT), Clinical and Experimental Allergy, 1999, vol. 29, pp. 896-904.

Valenta, R. and Niederberger, V., Recombinant Allergens for Immunotherapy, J. Allergy and Clinical Immunology, Apr. 2007, vol. 119, No. 4, pp. 826-830.

Valenta, R. et al., Component-Resolved Diagnosis to Optimize Allergen-Specific Immunotherapy in the Mediterranean Area, J. Investig Clin Immunol 2007, vol. 17, Supplement 1, pp. 88-92.

H.M.H. Van Eijk et al., Automated Isolation of High-Purity Plasma Albumin for Isotope Ration Measurements, Journal of Chromatography B, 731 (1999) pp. 199-205.

Bulone et al, Characterisation of Horse Dander Allergen Glycoproteins Using Amino Acid and Glycan Structure Analyses, Int Arch Allergy Immunol 2000; 123:220-227.

Jonas Lidholm, The Importance of Molecular Allergens for in Vitro Testing: A Critical Evaluation of Component-resolved Diagnostics, Arbeiten aus dem Paul-Ehrlich Institut, 12th International Paul-Ehrlich Seminar, Bad Homburg (2008).

Bulone et al, Separation of horse dander allergen proteins by two-dimensional electrophoresis molecular characterisation and identification of Equ c 2.0101 and Equ c 2.0102 as lipocalin proteins, Eur. J. Biochem. 253: 202-211 (1998).

Virtanen et al, Important Animal Allergens Are Lipocalin Proteins: Why Are They Allergenic?, Int Arch Allergy Immunol 1999; 120:247-248.

Fjeldsgaard B. E., Comparison of IgE-binding antigens in horse dander and a mixture of horse hair and skin scrapings, Allergy 1993, 48:535-541.

Mattsson et al, Purification and immunological characterization of horse dander allergens, Allergy, 63 (Suppl 88):281, Abstract No. 748 (2008).

English Translation of Official Action dated Mar. 26, 2015 from corresponding Japanese Application No. 2013-506115.

\* cited by examiner

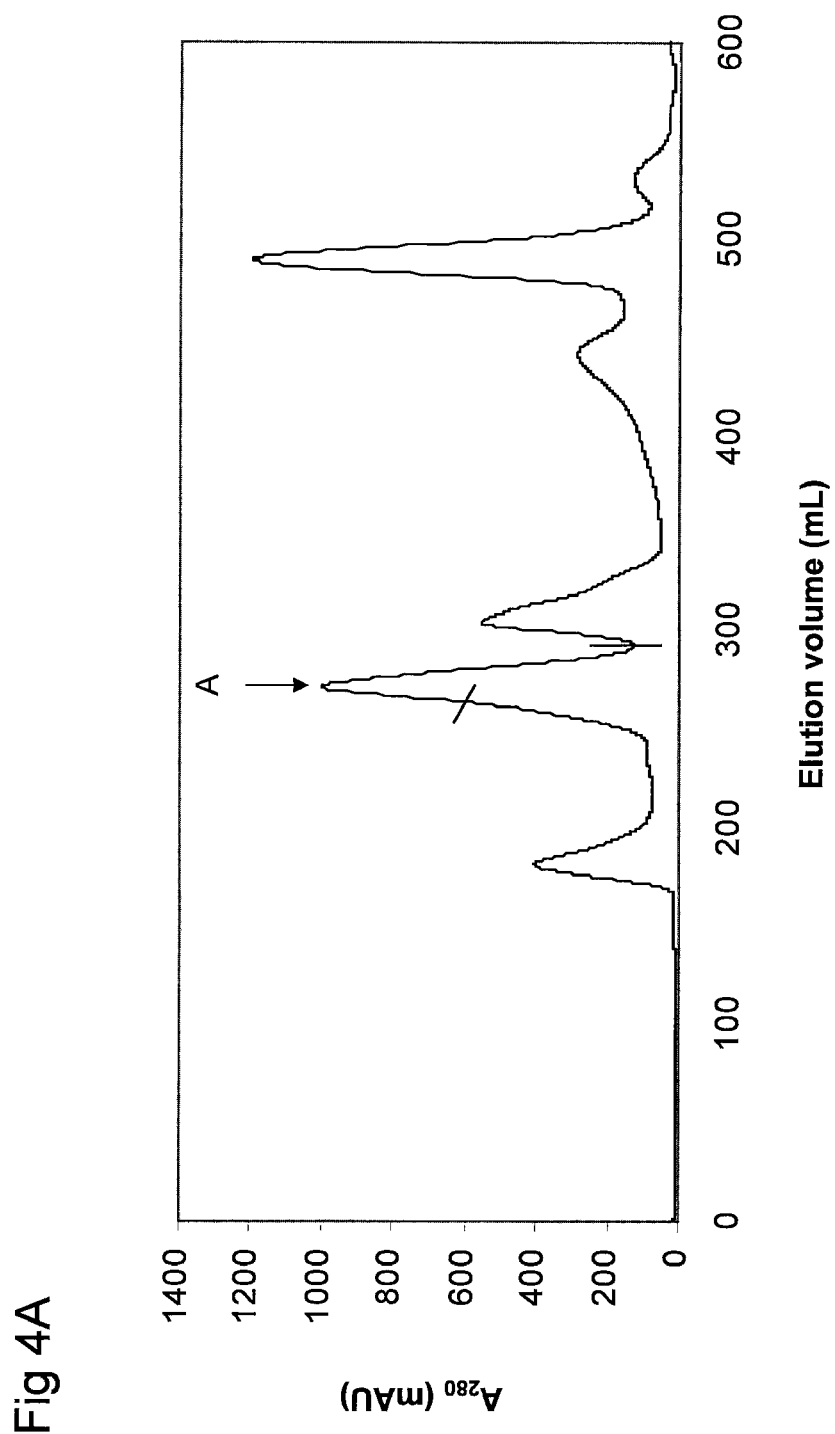

Fig 5

Equ c 15k - 5 kDa fragment

Predicted full length precursor sequence:

MRLFLPVLLVTLALCCCETNAATCPAVATDIASFFLLPDSLFKLQLIKYQAPPEAKDA

TMQVKQCINEISAGDRYIITETLGKIVLQCGA

Equ c 15k - 10 kDa fragment

Predicted full length precursor sequence:

MKLVTVLMLVAFPLYCYAGSGCQLLEDVVEKTITAELSPAEYVEAVQEFIPDEATEK

AAIQLKQCYLKQSNETLNDFRTMMNSMYNSAYCALF

ALLERGEN

RELATED APPLICATION

The present application is a 371 of PCT/SE2011/050503 filed Apr. 26, 2011.

SEQUENCE LISTING

The Sequence Listing submitted herewith, entitled 191641-May-23-2014_ST25.txt, created May 23, 2014 and having a size of 7289 bytes, is incorporated herein by reference.

FIELD OF THE INVENTION

The present invention relates to the field of allergy. More specifically, the invention relates to the identification of novel allergens from mammals and to diagnosis and treatment of allergy towards mammals.

BACKGROUND

Approximately 20% of the populations of the industrialized world become hypersensitive (allergic) upon exposure to antigens from a variety of environmental sources. Those antigens that induce immediate and/or delayed types of hypersensitivity are known as allergens (Breiteneder et al. 1997). These include products of grasses, trees, weeds, animal dander, insects, food, drugs and chemicals. The antibodies involved in atopic allergy belong primarily to the immunoglobulin E isotype (IgE). IgE binds to basophils mast cells and dendritic cells via a specific high affinity receptor FcεRI. Upon exposure to an allergen, allergen-specific IgE antibodies on the cell surface become cross linked leading to the release of inflammatory mediators such as histamine and leukotrienes resulting in physiological manifestations of allergy (Akdis 2006).

Diagnostic tests for allergy involve the detection of IgE antibodies from patients with a specificity to proteins from an allergen source. Typically, an aqueous extract from the allergen source, containing a mixture of proteins, is used in these tests. For most allergen sources, the allergenic proteins present in crude extract have only partly been identified and characterised. Diagnostic test procedures for detection of specific IgE antibodies in patients can either utilize an in vitro immunoassay using serum from the patient, or be a skin prick test (SPT), performed by topical application of the specific extract on the skin of the patient (Wainstein et al. 2007).

In recent years, many important allergenic proteins in the allergenic extracts have been identified and characterized. This has enabled the quantitation of specific IgE antibodies to each of these individual allergenic components, often referred to as component resolved diagnostics (CRD) (Valenta et al. 1999) (Hiller et al. 2002) which in many cases can lead to an improved diagnosis of hypersensitivity (Stumvoll et al. 2003). The use of CRD has also been suggested as an aid in the selection of optimal immunotherapy treatment (Valenta et al. 2007). Further, individual allergens can in some cases be used to enhance the diagnostic sensitivity of an extract by spiking the extract with a component. In conclusion, it is thus of great importance to identify and characterise all important allergenic proteins in each allergen source.

Apart from reducing symptoms of allergy by e. g. antihistamines, more long-term and curative treatment of allergy can be performed with specific immunotherapy. Application of the disease causing allergenic extract, most commonly either subcutaneously or sublingually, that causes a specific activation of a protective immune response to the allergenic proteins. Although the exact mechanisms are not fully known, such a specific activation of the immune system alleviates the symptoms of allergy upon subsequent environmental exposure of the same allergen (Akdis et al. 2007). A further development of regular immunotherapy has been to use one or several purified allergenic proteins instead of a crude natural extract. Such immunotherapy has been successfully performed for grass pollen allergic patients (Jutel et al. 2005) and it has also been suggested for treating allergy against animal dander (Gronlund et al. 2009).

Horse dander is an increasingly common cause of respiratory allergy (Liccardi et al. 2011), with symptoms including rhinitis, conjunctivitis, bronchial inflammation and asthma. Occupational exposure to horse allergens is a significant risk factor for allergic sensitisation (Tutluoglu et al. 2002) but considerable concentrations of allergens can be detected also in other places such as schools (Kim et al. 2005). IgE sensitisation to horse dander was in one study shown to be associated with a high risk of developing asthma (Ronmark et al. 2003).

Extracts of horse hair and dander contain a complexity of allergenic proteins and four horse allergens have so far been identified: Equ c 1, Equ c 2, Equ c 3 and Equ c 4/5. The first two are both members of the lipocalin protein family and have been purified from their natural source (Dandeu et al. 1993; Goubran Botros et al. 1998) while only Equ c 1 has been expressed as a recombinant protein (Gregoire et al. 1996). The amino acid sequence of Equ c 1 is 67% similar to that of the cat allergen Fel d 4 (Smith et al. 2004). Equ c 3, horse serum albumin, is a relatively conserved protein showing extensive cross-reactivity to other mammalian albumins (Goubran Botros et al. 1996). Equ c 4/5, was first purified and reported as an IgE binding protein in horse dander (Goubran Botros et al. 1998; Goubran Botros et al. 2001) and only later identified as horse sweat latherin (McDonald et al. 2009). Equ c 1 is claimed to be the most important one of the known horse allergens (Dandeu et al. 1993) and IgE antibody recognition of the recombinant protein was present in 76% of a population of horse allergic subjects studied (Saarelainen et al. 2008). In another study using purified native allergens, only 33% of horse allergic patients were sensitized to Equ c 2 and 23% to Equ c 4/5 (Goubran Botros et al. 1998). The frequency of IgE binding to horse serum albumin has been addressed in several studies demonstrating reactivity in up to 40% of horse allergic subjects (Spitzauer et al. 1993; Cabañas et al. 2000). However, as sensitization to serum albumins is often accompanied by higher concentrations of IgE antibodies to other allergen components, its specific clinical relevance is uncertain.

Although the horse dander allergens Equ c 1, Equ c 2, Equ c 3 and Equ c 4/5 have been known for a long time, no quantitative estimation of each component's contribution to the total IgE response to horse dander has been made.

SUMMARY OF THE INVENTION

As stated above, a well designed laboratory immunoassay for specific IgE antibodies can detect most cases of sensitization to horse using natural horse dander extract. However, in a miniaturized or non-laboratory immunoassay, such as an allergen microarray or a doctor's office test, the combination of less favourable assay conditions, lower capacity for antibody-binding allergen reagent and natural allergen extract of limited potency, may cause insufficient diagnostic sensitivity. A similar situation may exist also for immunoassays for specific IgE to other animal epithelia. Thus, there is a need in some cases to use pure allergenic proteins to achieve sufficient sensitivity in diagnostic tests for specific IgE antibodies to animal epithelia.

Such allergens may be useful not only as reagents for increased sensitivity in routine diagnostic tests, but also in different types of component-resolved diagnostic applications (Valenta et at 1999) (Hiller et al. 2002). Pure allergenic proteins, or fragments and variants thereof with improved non-anaphylactic properties, may also be used as novel reagents in immunotherapy (Valenta et al. 1999) (Cromwell et al. 2006) (Saarne et al. 2005); (Jutel et al. 2005); (Cromwell et al. 2006).

The purification and analysis of all the known horse allergen components resulted in the identification of some patients' sera having a significantly higher IgE response to horse dander extract than could be collectively accounted for by the sum of the individual horse allergen components. These sera were found to have IgE binding reactivity to a previously unknown horse allergen component.

With the aid of the sera described above, a new major allergen could be purified from horse dander and identified as a member of the secretoglobin protein family. The novel horse protein, herein referred to as Equ c 15k, consists of one 5 kDa amino acid chain and one 10 kDa amino acid chain joined together by disulfide bridges. Considering the fact that the two polypeptide chains are encoded by separate genes, this study demonstrates the presence of a heterodimeric protein that has not previously been anticipated by bioinformatic studies of the horse genome. It is in all aspects distinct from previously known horse allergens. This allergen represents an important addition to the panel of known horse allergens and will be useful in the diagnosis of horse allergy.

In one aspect the present invention relates to an isolated horse allergen, Equ c 15k belonging to the secretoglobin family, showing an electrophoretic mobility (apparent molecular weight) corresponding to approximately 15 kDa under non-reducing conditions, and comprising a first peptide chain having a molecular weight in the order of 5 kDa and a second peptide chain having a molecular weight in the order of 10 kDa, linked together by one or more disulfide bonds. This aspect of the invention also comprises variants and fragments of Equ c 15k, sharing epitopes for antibodies therewith, such that the variants and fragments cross-react with such antibodies to at least about 50%. Such variants and fragments include, for example, related allergens from the same species. Also in the other aspects of the invention described below, the term "Equ c 15k" is, for simplicity, used to also include such variants and fragments thereof.

In another aspect, the invention relates to an isolated nucleic acid encoding the allergen according to the first-mentioned aspect, as well as to a vector containing the nucleic acid molecule, and to a host cell containing the vector. Recombinant proteins or peptides produced by such a vector-containing host cell may be glycosylated or not depending on the host cell used.

In a further aspect, the invention relates to the use of Equ c 15k for the manufacture of a composition for diagnosis of Type I allergy.

In a further aspect, the invention relates to an allergen composition "spiked" with Equ c 15k. Such an allergen composition may be an allergen extract or a mixture of purified or recombinant allergen components having no or a low Equ c 15k content, wherein Equ c 15k is added in order to bind IgE from patients whose IgE would not bind, or bind poorly, to the other allergen components in the composition. This aspect of the invention also relates to a method for producing such a composition, which method comprises the step of adding Equ c 15k to an allergen composition, such as an allergen extract (optionally spiked with other components) or a mixture of purified native or recombinant allergen components.

In yet a further aspect, the invention relates to an in vitro diagnostic method for diagnosing a Type I allergy in a patient, wherein a body fluid sample, such as a blood or serum sample from the patient, is brought into contact with Equ c 15k or a composition according to the previous aspect, whereby it can be determined whether or not the patient sample contains IgE antibodies that bind specifically to the Equ c 15k. Such a diagnostic method may be carried out in any manner known in the art. The Equ c 15k may e.g. be immobilized on a solid support, such as in a conventional laboratory immunoassay, in a microarray or in a lateral flow assay, or used as a fluid-phase reagent.

In another aspect, the invention relates to a diagnostic kit for performing the method according to the previous aspect.

In the above mentioned aspects, the wildtype Equ c 15k molecule may, as mentioned above, be replaced with fragments or variants of Equ c 15k, natural or man-made, sharing epitopes for antibodies with the wildtype protein, as defined below.

The invention further relates to a method of treatment of Type I allergy comprising administering to a patient in need of such treatment Equ c 15k or a modified Equ c 15k, as explained below. This aspect of the invention also relates to the use of the Equ c 15k in such immunotherapy, including e.g. component-resolved immunotherapy (Valenta et al. 2007). In one embodiment of this aspect, the Equ c 15k may be used in its natural form or in a recombinant form displaying biochemical and immunological properties similar to those of the natural molecule. In another embodiment, the Equ c 15k may be used in a modified form, generated chemically or genetically, in order to abrogate or attenuate its IgE antibody binding capacity, while preferably being capable of eliciting an IgG response in a treated individual. Examples of modifications include, but are not limited to, fragmentation, truncation, tandemerization or aggregation of the molecule, deletion of internal segment(s), substitution of amino acid residue(s), domain rearrangement, or disruption at least in part of the tertiary structure by disruption of disulfide bridges or its binding to another macromolecular structure, or other low molecular weight compounds. In yet another embodiment of this aspect, the individual 10 kDa and/or 5 kDa subunits of Equ c 15k, which display reduced IgE binding activity as compared to the intact molecule, are used as modified Equ c 15k.

In all of the above mentioned aspects of the invention, the Equ c 15k protein may be purified from its natural source, such as from urine, saliva or other body fluids, or from tissue, such as hair or dander, from horse. It may also, as mentioned above, be produced by recombinant DNA technology or chemically synthesized by methods known to a person skilled in the art.

The invention also relates to the Equ c 15k for use in prophylactic or therapeutic treatment of Type 1 allergy, as well as in diagnosis.

DEFINITIONS

The allergenic horse protein described here, Equ c 15k, belongs to the secretoglobin protein family, specifically one subfamily which comprises tetrameric proteins formed by two heterodimeric subunits. The heterodimer consists of two chains derived from different genes linked together by disulfide bridges (Klug et al. 2000). The horse secretoglobin described here is a 15 kDa heterodimer, herein referred to as Equ c 15k, consisting of a 5±2 kDa and a 10±2 kDa subunit, respectively, which for the purposes of this invention are referred to as the 5 and 10 kDa subunits, respectively. The molecular weight assignments are according to their apparent molecular weight as observed in SDS-PAGE, as described in Example 4 below. It is understood that the apparent molecular weights will vary depending on the separation conditions, including electrophoretic separation medium and concentration thereof, linear or gradient buffer used, etc. Also, the 10 kDa subunit contains an N-glycosylation site, the occupation of which by a glycan structure may affect the apparent molecular weight.

The amino acid sequence of the 5 kDa chain has the predicted amino acid sequence ATCPAVATDIASFFLLPD-SLFKLQLIKYQAPPEAKDATMQVKQCINEIS AGDRYI-ITETLGKIVLQCGA (SEQ ID NO: 4) and a theoretical molecular weight of 7.5 kDa.

The amino acid sequence of the 10 kDa chain has the predicted amino acid sequence GSGCQLLEDVVEKTI-TAELSPAEYVEAVQEFIPDEATE-KAAIQLKQCYLKQSNETLNDFR TMMNSMYNSAY-CALF (SEQ ID NO: 5) and a theoretical molecular weight of 8.4 kDa.

It is to be noted that structurally related proteins have been described in a wide range of mammalian species but only one protein has been defined as an allergen, i.e. the major cat allergen Fel d 1 (Acc no P30438 and P30440).

Variants and fragments of Equ c 15k should be construed as meaning proteins or peptides with a length of at least 10 amino acids, more preferably at least 40, even more preferably at least 50 or 60 amino acid residues of each chain in the heterodimer, and a sequence identity to said Equ c 15k of at least 50%, preferably over 60%, 70%, 80%, 90% or 95%.

A modified Equ c 15k should in the context of the present invention be construed as meaning an Equ c 15k variant that has been chemically or genetically modified to change its immunological properties, e.g. as exemplified above in relation to the immunotherapy aspect of the invention.

Variants and fragments of Equ c 15k sharing epitopes for antibodies with Equ c 15k should be construed as being those fragments and variants whose binding of antibodies, such as IgE or IgG antibodies, from a serum sample from a representative Equ c 15k sensitized patient can be significantly inhibited by Equ c 15k. Such an inhibition assay may e.g. be performed according to the methods described by (Mattsson et al. 2009) (the disclosure of which is incorporated by reference herein).

A hypoallergenic modified Equ c 15k or variant or fragment of Equ c 15k should be construed as being a modified Equ c 15k or variant or fragment of Equ c 15k that is not capable of binding Equ c 15k reactive IgE antibodies from a serum sample of a representative Equ c 15k sensitized patient, as determined e.g. by the protocol according to Example 7 below or which displays no or significantly reduced biological allergen activity, as determined by a cellular activation assay such as the basophil histamine release assay (Demoly et al. 2003; Ebo et al. 2004).

BRIEF DESCRIPTION OF DRAWINGS

FIG. 5 shows the predicted sequence of the 5 kDa (SEQ ID NO: 6) and 10 kDa (SEQ ID NO: 7) amino acid chains of nEqu c 15k. Amino acids identified by N-terminal sequencing are underlined and amino acids identified by MS/MS analysis are shown in bold.

DETAILED DESCRIPTION OF THE INVENTION

The examples below illustrate the present invention with the isolation and use of secretoglobin from horse. The examples are only illustrative and should not be considered as limiting the invention, which is defined by the scope of the appended claims.

Example 1

Purification and Characterisation of Known Allergens from Horse Dander and Serum Horse dander was used as a starting material for purification of Equ c 1, Equ c 2 and Equ c 4/5 while Equ c 3 was purified from horse serum.

Horse dander (Allergon, Välinge, Sweden) was extracted in 20 mM MOPS, pH 7.6, 0.5 M NaCl (MBS=MOPS-buffered saline), clarified by centrifugation and filtered through a 0.45 μm mixed cellulose ester filter (Millipore, Billerica, Mass., USA). As a first purification step for all three horse dander allergens, the clarified extract was applied to a Superdex™ 75 column (XK26/100, $V_t$=505 mL, GE Healthcare Life Sciences, Uppsala, Sweden) for size exclusion chromatography (SEC) and elution was performed with MBS at a flow rate of 2 mL/min.

Equ c1

Figure 1A:
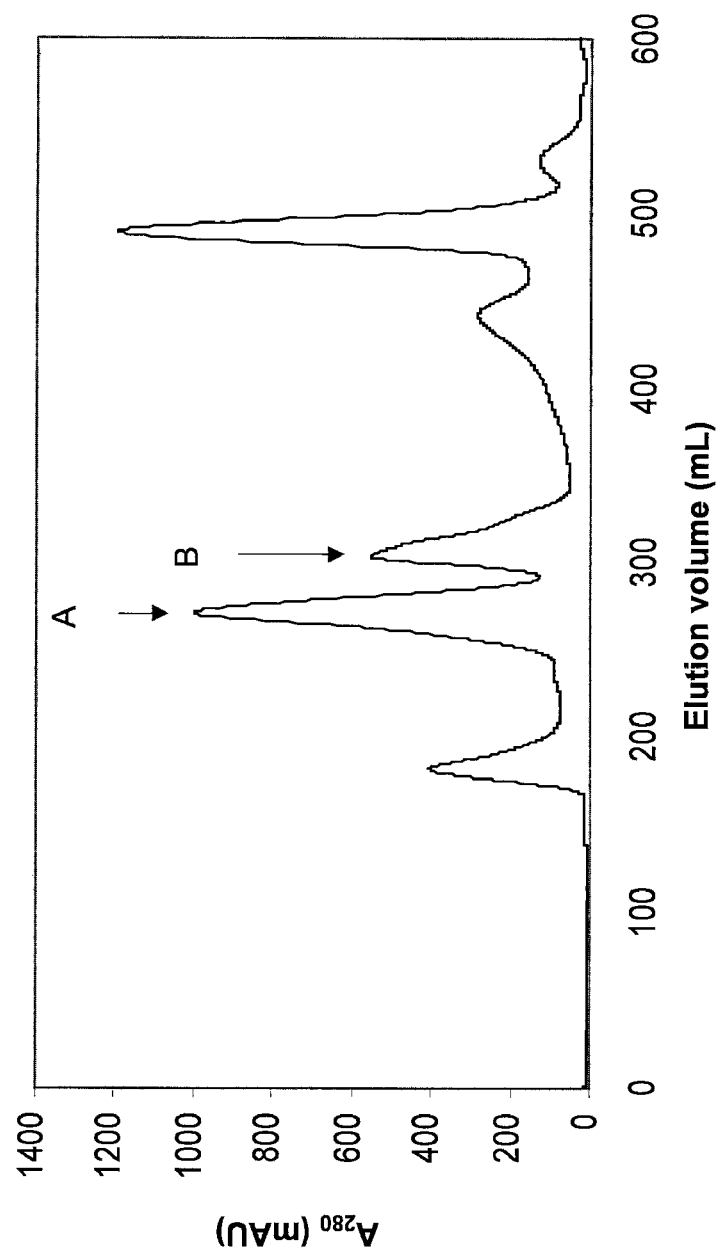
FIG. 1A shows the fractionation of horse dander proteins by size exclusion chromatography (SEC). Peaks A and B that were used for subsequent purification steps are indicated by arrows.
Figure 1B:
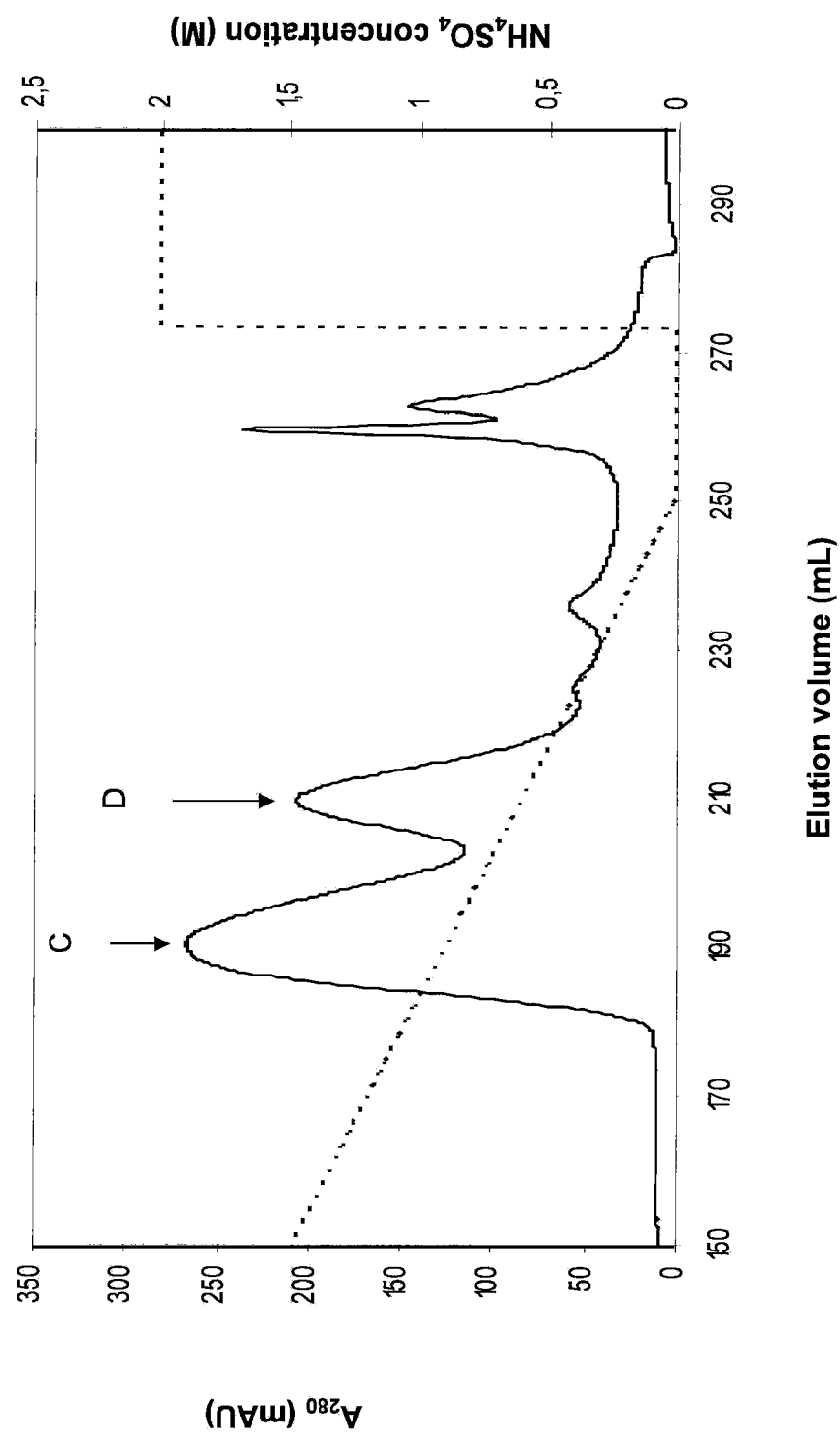
FIG. 1B shows the purification of nEqu c 1 by hydrophobic interaction chromatography. Peaks C and D were used for subsequent purification steps.
Figure 1C:
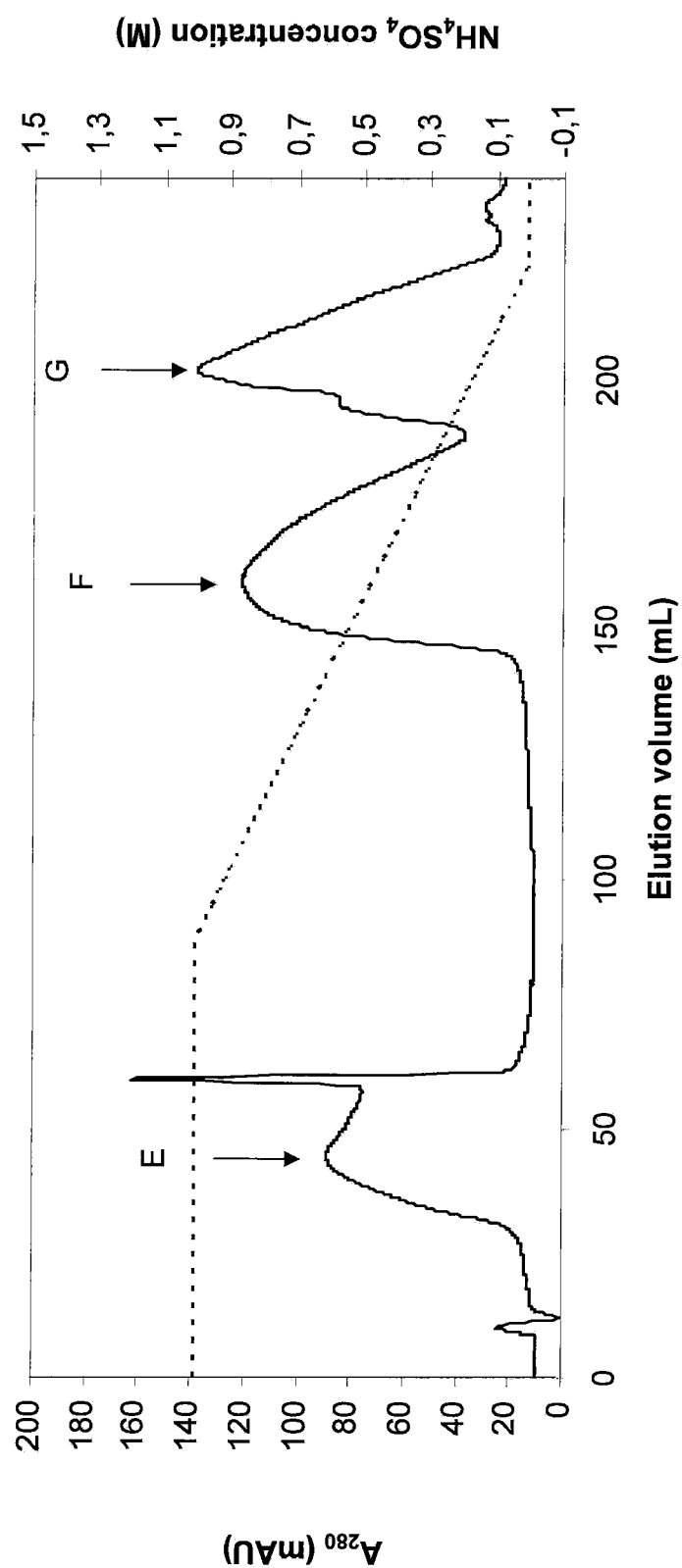
FIG. 1C shows the purification of nEqu c 2 and Equ c 4/5 by hydrophobic interaction chromatography. Peaks E, F and G were used for subsequent purification steps.
Figure 1D:
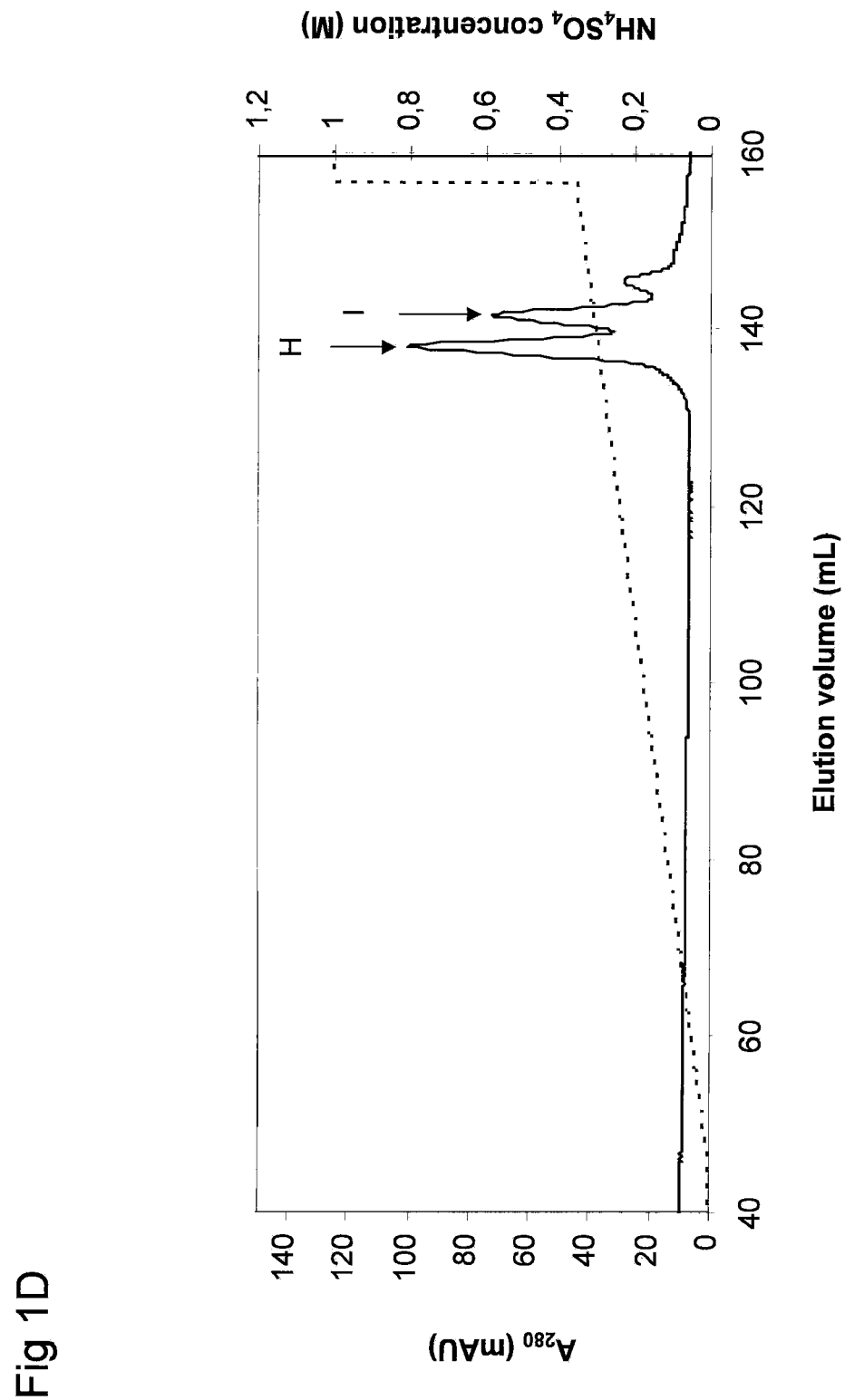
FIG. 1D shows the purification of nEqu c 2 by anion exchange chromatography. Peaks H and I were used for subsequent analysis.
Figure 1E:
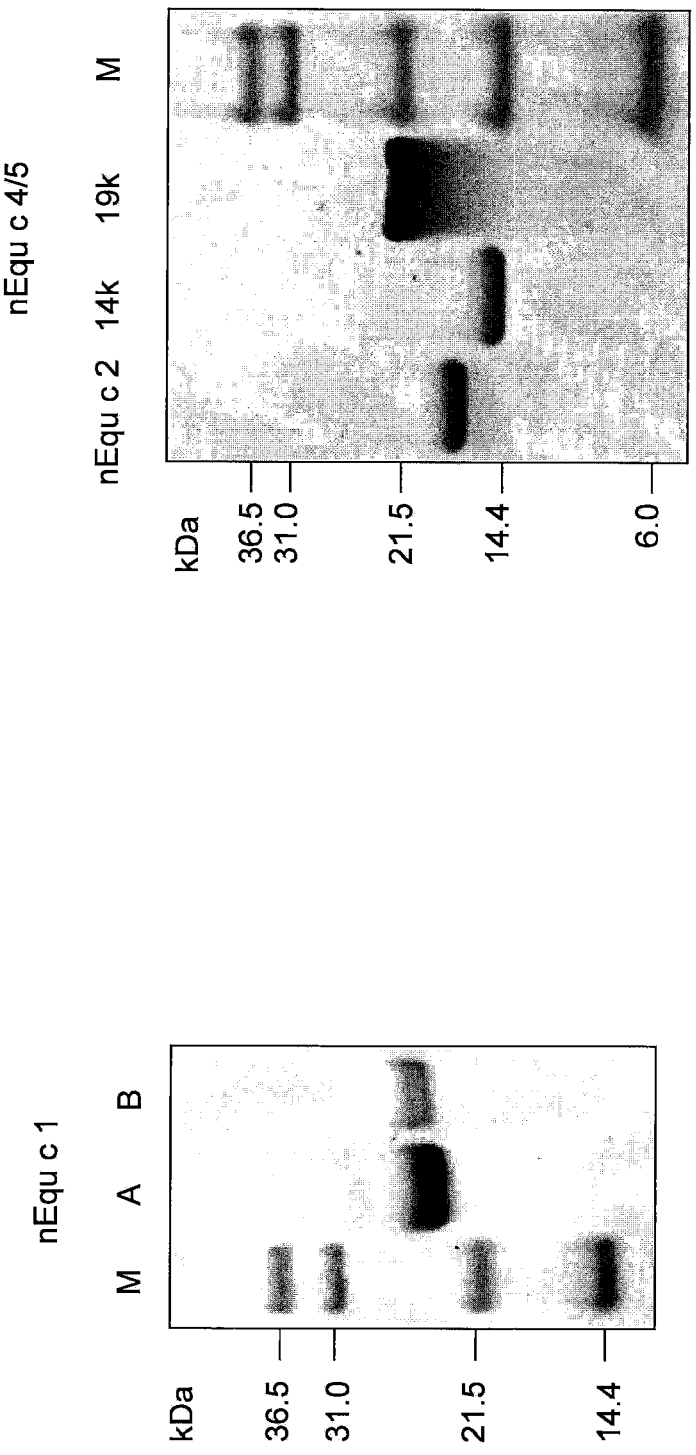
FIG. 1E shows SDS-PAGE analysis of the purified proteins Equ c 1 forms A and B, Equ c 2 and Equ c 4/5 form 14 kDa and 19 kDa. Lane M contains molecular weight marker proteins with the molecular weight indicated to the left.

In order to purify Equ c 1, peak A in FIG. 1A was adjusted to 2 M $NH_4SO_4$ and applied to a Phenyl Sepharose™ HP column (HR10/10, $V_t$=9.0 mL, GE Healthcare Life Sciences) equilibrated with 2 M $NH_4SO_4$ in 20 mM tris pH 8.0. Elution was performed in a linear $NH_4SO_4$ gradient from 2 M to 0 M $NH_4SO_4$. Two peaks containing Equ c 1 were eluted in the middle of the gradient, peaks C and D in FIG. 1B. After desalting each peak on a Sephadex™ G25 fine column (XK16/20, $V_t$=34 mL, GE Healthcare Life Sciences) equilibrated with 20 mM MOPS pH 7.6 0.5 M NaCl, each preparation of of nEqu c 1 was subjected to sodium dodecyl sulfate polyacrylamide gel electrophoresis (SDS-PAGE) using the NuPAGE MES buffer system (10% NuPAGE gel, Invitrogen, Carlsbad, Calif., USA) of a reduced sample prepared by mixing the sample 1:3 with NuPAGE LDS sample buffer (Invitrogen) containing 100 mM β-mercaptoethanol. As an indication of apparent molecular weight the Mark 12™ standard (Invitrogen) was used. Both nEqu c 1 preparations were pure as judged by SDS-PAGE (FIG. 1E).

The protein preparations was unambiguously identified as Equ c 1 by peptide mass fingerprinting (PMF) performed in a Bruker Daltonics Autoflex 2 instrument (Bruker Daltonics, Bremen, Germany) as described in (Mattsson et al. 2009). Both forms of the protein were immobilized to Immuno-CAP™ solid phase as described (Marknell DeWitt et al. 2002).

Equ c 2

In order to purify Equ c 2, the second peak from SEC, peak B in FIG. 1A, was adjusted to 1 M $NH_4SO_4$ and subjected to hydrophobic interaction chromatography (HIC) on a phenyl Sepharose™ HP column (HR10/10, $V_t$=9.0 mL, GE Healthcare Life Sciences) equilibrated with 1 M $NH_4SO_4$ in 20 mM Tris pH 8.0. Elution was performed in a linear $NH_4SO_4$ gradient from 1 M to 0 M $NH_4SO_4$ in the same buffer. Equ c 2 was contained in the flow through fraction (peak E in FIG. 1C) that was pooled and desalted on a Sephadex™ G25 fine column (XK26/20, $V_t$=90 mL, GE Healthcare Life Sciences) equilibrated with 20 mM Bis-Tris propane, pH 8.5. The desalted Equ c 2 pool was finally applied to an anion exchange column Source™ 15Q (HR16/10, $V_t$=9 mL, GE Healthcare Life Sciences) equilibrated with 20 mM Bis-Tris propane, pH 8.5. Upon elution in a linear 0-0.40 M NaCl gradient in the same buffer, the protein was resolved into three peaks that all displayed pure 17 kDa band upon SDS-PAGE analysis. The two largest peaks were analysed by N-terminal sequencing (Procise™ LC452, Applied Biosystems, Foster City, Calif., USA) and both had the sequence DQDPQSEDTY (SEQ ID NO: 10), identifying them as Equ c 2.0201 (FIG. 1D peaks H and I). For the purpose of evaluating IgE binding reactivity, the peaks were pooled and immobilised to ImmunoCAP™ solid phase as described (Marknell DeWitt et al. 2002).

Equ c 4/5

Purification of Equ c 4/5 was performed by using the second peak from SEC, peak B in FIG. 1A. This pool was adjusted to 1 M $NH_4SO_4$ and subjected to hydrophobic interaction chromatography (HIC) on a phenyl Sepharose™ HP column (HR10/10, $V_t$=9.0 mL, GE Healthcare Life Sciences) equilibrated with 1 M $NH_4SO_4$ in 20 mM Tris pH 8.0. Elution was performed in a linear $NH_4SO_4$ gradient from 1 M to 0 M $NH_4SO_4$ in the same buffer. Equ c 4/5 protein eluted in two distinct peaks in the middle of the gradient, (peaks F and G in FIG. 1C). SDS-PAGE analysis of the first peak revealed a protein migrating as a 14 kDa band while the second peak contained a 19 kDa band. After desalting on a Sephadex™ G25 fine column (XK26/20, $V_t$=90 mL, GE Healthcare Life Sciences) equilibrated with 20 mM Bis-Tris propane, pH 8.5. Both proteins were pure as judged by SDS-PAGE (FIG. 1E). Both of the two preparations displayed the N-terminal sequence VGPLLGPSDA (SEQ ID NO: 11), identifying them as horse latherin or Equ c 4/5.

The two forms of nEqu c 4/5 were immobilized separately to ImmunoCAP™ solid phase as described (Marknell DeWitt et al. 2002).

Equ c 3

Native Equ c 3 was purified from horse serum by affinity chromatography using Blue Sepharose FF, (GE Healthcare Life Sciences), anion exchange chromatography (AIEC) and SEC essentially as described (van Eijk et al. 1999).

Example 2

Figure 2A:
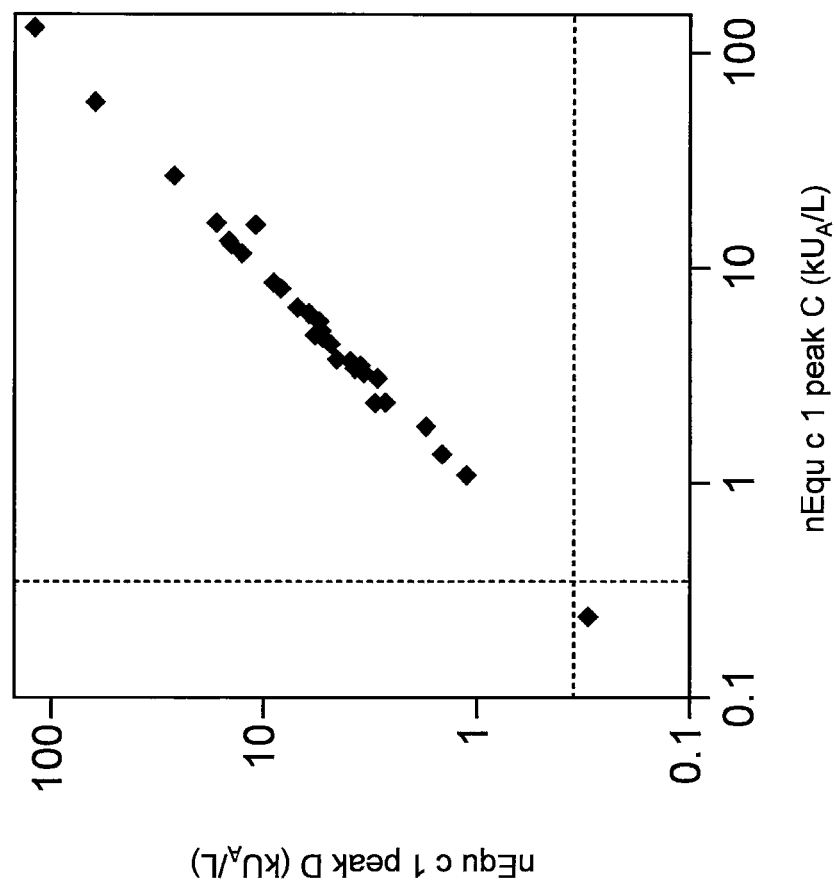
FIG. 2A compares the IgE binding of the two forms, A and B, of nEqu c 1 (from peak C and peak D respectively) using 35 horse dander reactive sera. Dotted lines indicate the 0.35 $kU_A/L$ cut-off level.
Figure 2B:
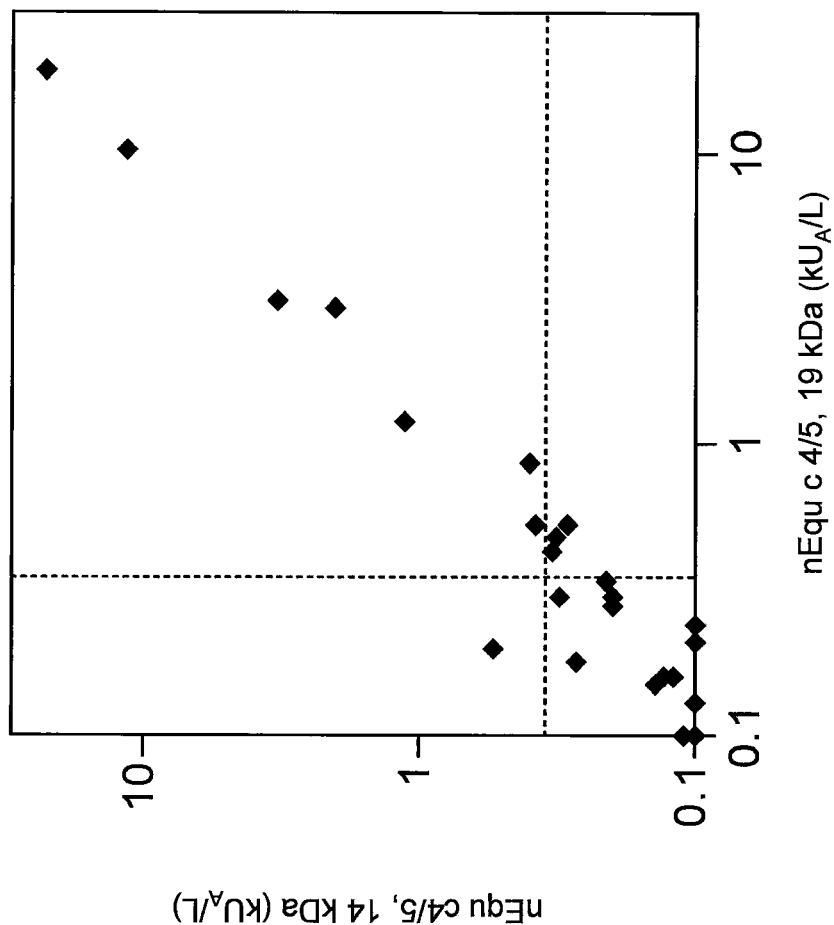
FIG. 2B compares the IgE binding of the 19 kDa and the 14 kDa forms of nEqu c 4/5 using 38 horse dander reactive sera. Dotted lines indicate the 0.35 $kU_A/L$ cut-off level.

Assessment of IgE Binding Levels to Individual Horse Dander Allergen Components in a Panel of Sera from Horse Sensitized Individuals The IgE binding activity of the two forms of Equ c 1, named form A and B, was evaluated using a set of horse dander sensitized sera (obtained from an in-house serum collection. The two forms of Equ c 1 displayed equivalent IgE binding activity, as shown in FIG. 2A. Therefore only the values obtained with nEqu c 1 A were used in the analysis below. Using a similar set of horse dander reactive sera, IgE antibody binding to the two forms of Equ c 4/5 were compared and found to be very similar, as shown in FIG. 2B.

IgE antibody binding to horse dander extract and the purified horse allergens was examined using regular and experimental ImmunoCAP™ tests (Phadia, Uppsala, Sweden). Experimental ImmunoCAP™ tests were prepared as described above. A panel of 29 sera from horse dander sensitised individuals were used. Determinations of IgE responses to horse dander extract, nEqu c 1, nEqu c 2, nEqu c 4/5 and were performed. The results are presented in Table 1 where the IgE antibody concentrations in sera of patients A1 to A29 to HDE and the components and sum of the three components are displayed as $kU_A/L$. The component coverage is the ratio of component sum and horse dander extract, expressed as percentage. A number of sera were identified as having a significantly higher level of IgE binding to horse dander extract than could be accounted for by the individual components, e.g. sera no A1, A21 and A22. Apart from possible Equ c 3 reactivity, which was not evaluated at this stage, the identified sera could aid in the search for novel IgE binding proteins from horse dander.

Example 3

Figure 3A:
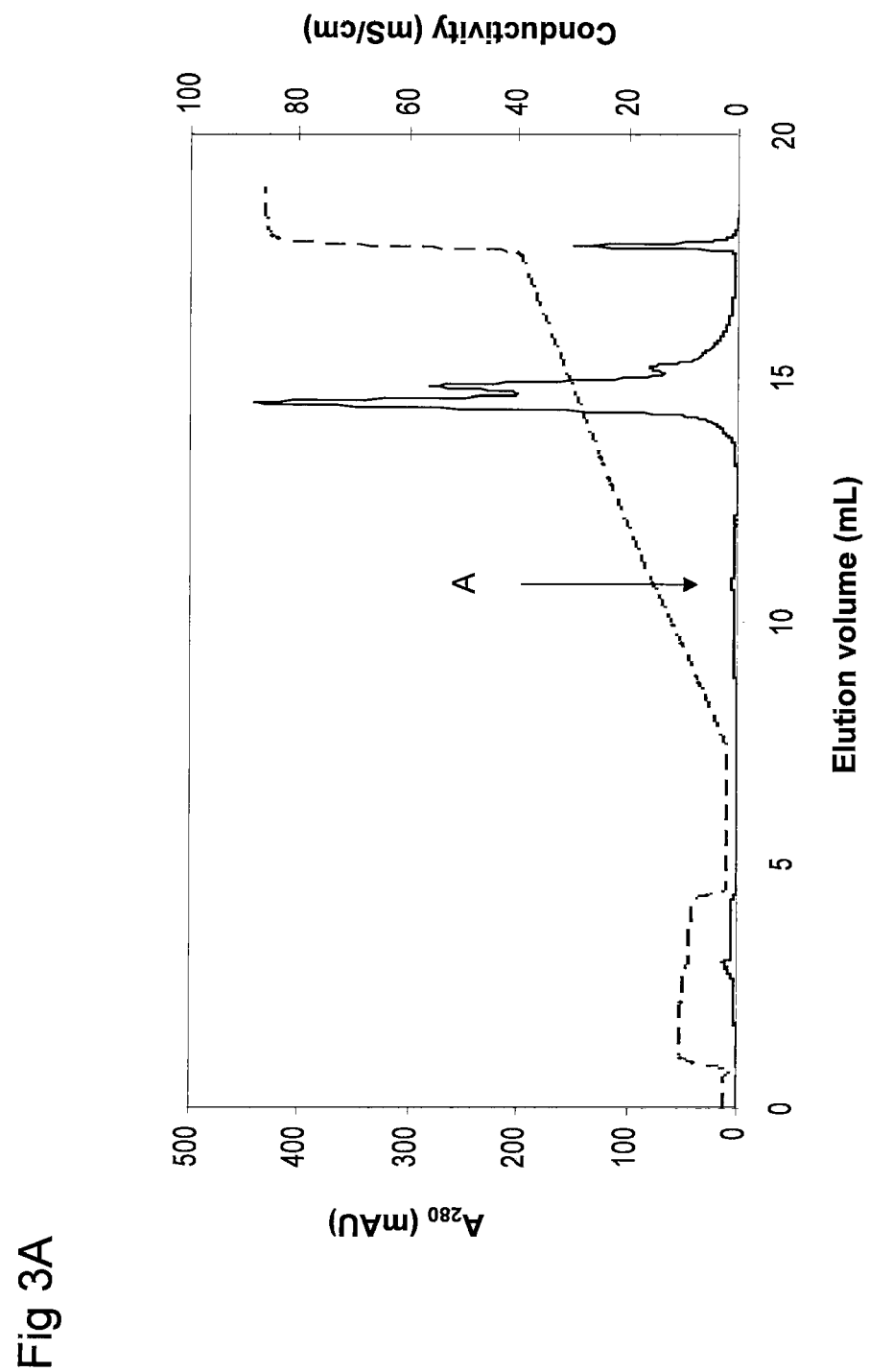
FIG. 3 shows the purification of fractions used to search for novel IgE binding proteins. A: Purification of fraction A by anion exchange chromatography. B: Purification of fractions B and C by hydrophobic interaction chromatography.
Figure 3B:
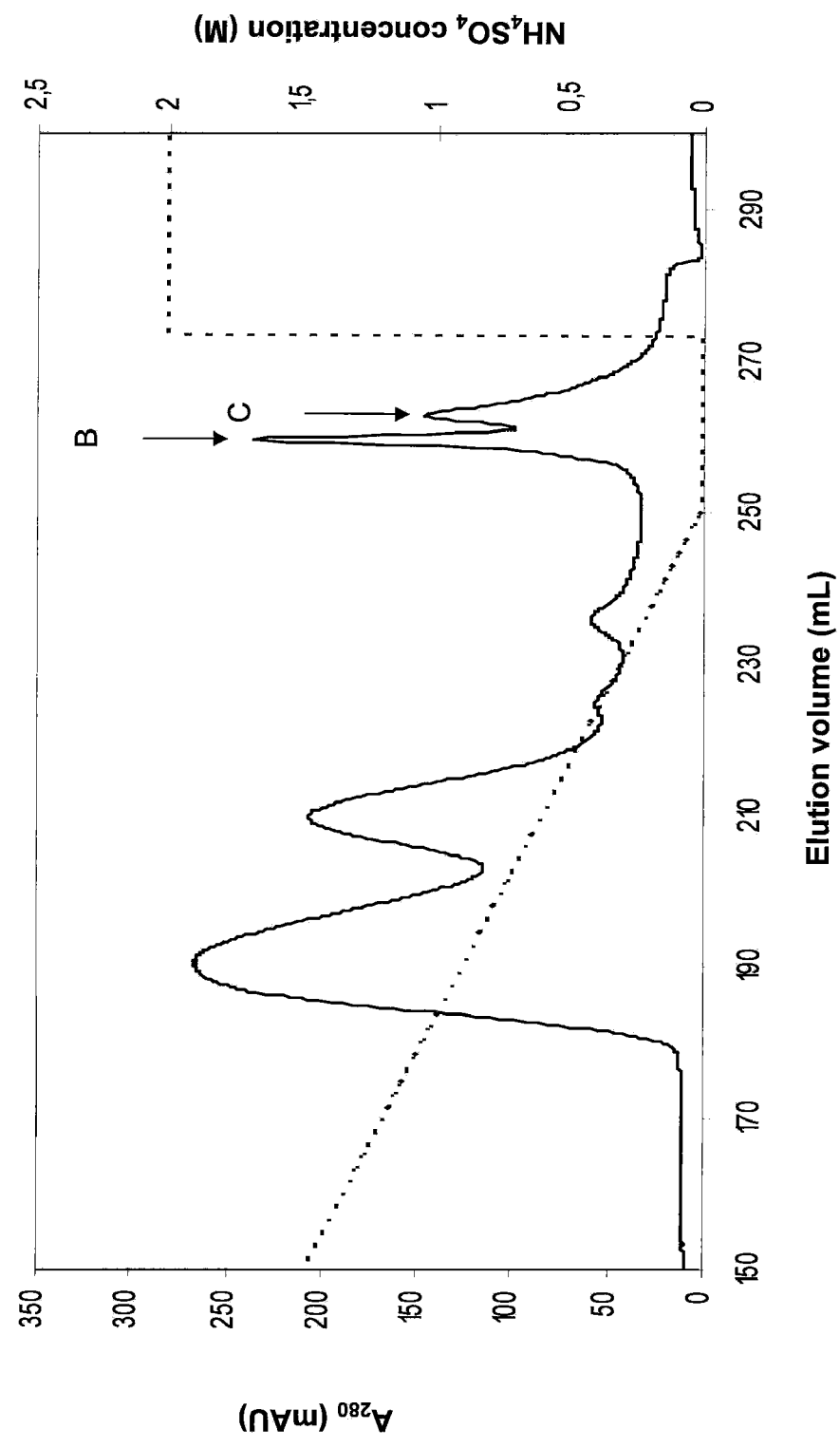

Identification of a Fraction from Horse Dander Having a Novel IgE Binding Reactivity During the process of purifying the previously characterised horse dander allergens, several fractions were identified which contained proteins other than the previously known horse allergens. Three fractions of particular interest were selected for analysis of IgE binding activity using the sera identified in Example 2 above. Fraction A contained a 10 kDa band (reducing SDS-PAGE) obtained from an anion exchange purification step of Equ c 2 indicated by an arrow (FIG. 3A). Fractions B and C, containing a 13 kDa and a 10 kDa band (reducing SDS-PAGE), respectively, were obtained from a HIC purification step of Equ c 1 and are indicated by arrows in FIG. 3B. Experimental ImmunoCAP™ (Phadia) tests were prepared as described (Marknell DeWitt et al. 2002) and used for serum analysis.

The results are summarised in Table 2, which also includes the previous determinations of horse dander extract and the sum of nEqu c 1, nEqu c 2 and nEqu c 4/5, all displayed as $kU_A/L$. The highest IgE binding levels were found in fraction C. Notably, in serum A1, the level of IgE binding to fraction C was much higher than the sum of IgE binding to nEqu c 1, nEqu c 2 and nEqu c 4/5. The fact that this serum had an albumin IgE reactivity of only 1.5 kUA/L (not shown) suggested that fraction C contained a novel horse dander allergen.

Example 4

Figure 4B:
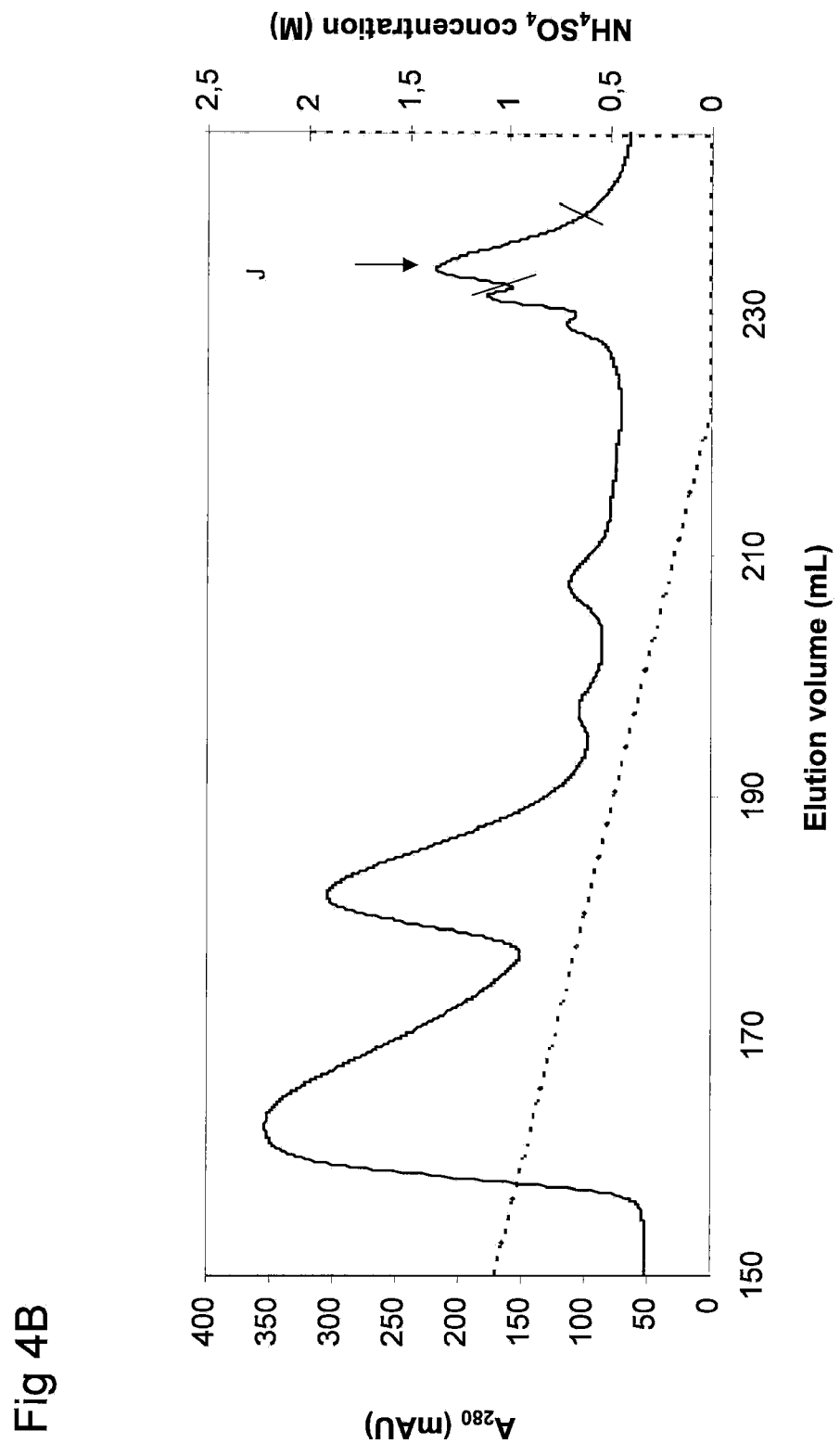
FIG. 4 shows the purification of a 15 kDa horse dander protein. A: Fractionation of horse dander extract by size exclusion chromatography. Peak A was used for subsequent purification steps. B: Fractionation of peak A by hydrophobic interaction chromatography. Peak J, pooled as indicated in the figure, was used for subsequent purification steps. C: Fractionation of peak J by anion exchange chromatography. Peaks K and L were used for subsequent analysis and/or further purification steps. D: shows SDS-PAGE analysis reduced (Red) and non-reduced (Ox) samples of the purified 15 kDa horse dander protein. Lane M contains molecular weight marker proteins with the molecular weight indicated to the left. E: Refining purification of peak K by reversed-phase chromatography. Peak M was used for subsequent immunological analysis.
Figure 4C:
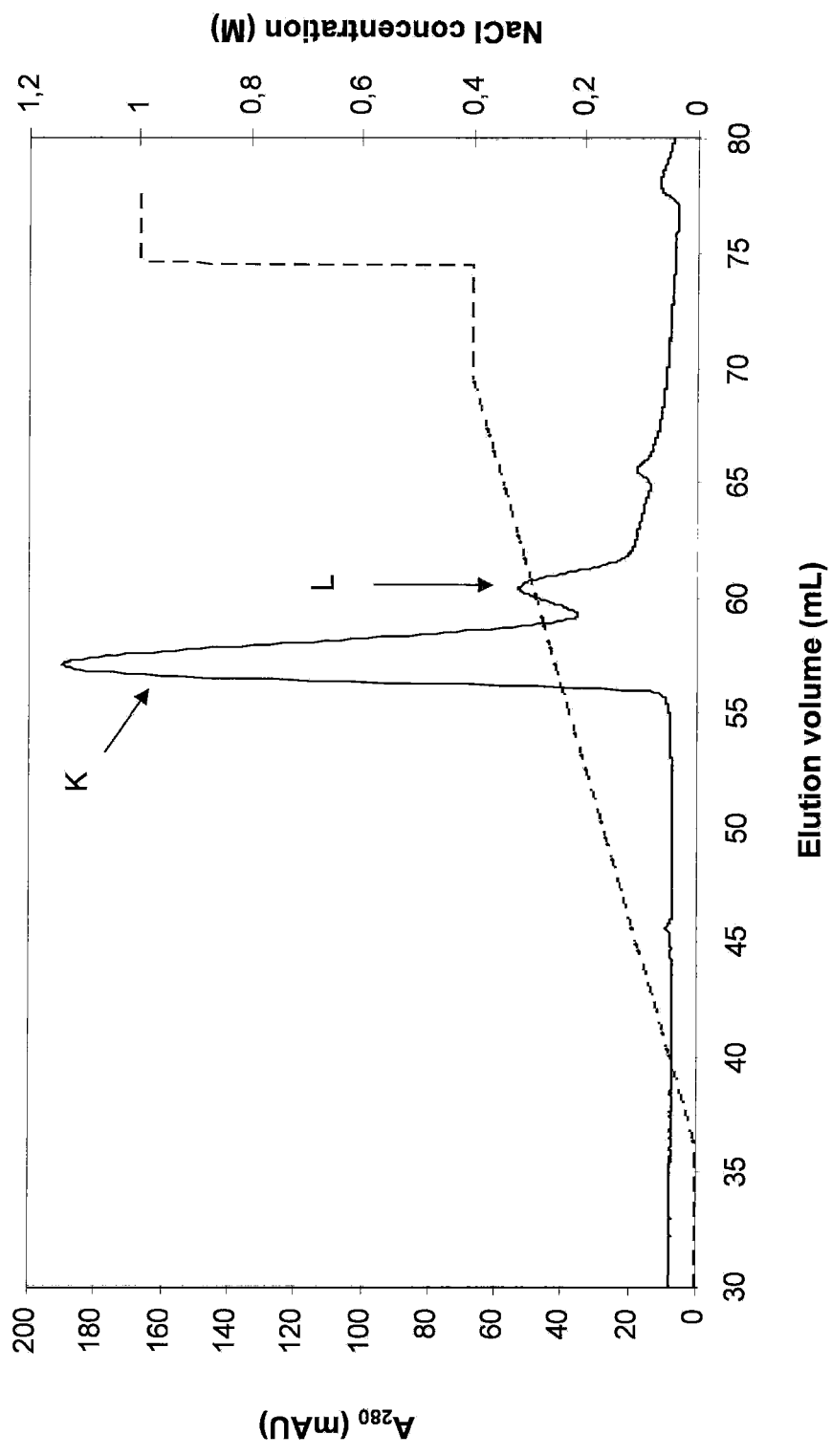

Purification and Identification of the Dominant Protein Constituent of Fraction C Purification of a Horse Dander Protein from Fraction C To purify the 10 kDa protein present in fraction C in a more targeted way, horse dander extract was subjected to SEC as described in Example 1. The Equ c 1 containing peak was pooled according to SDS-PAGE analysis as indicated in the figure (peak A in FIG. 4A). Only the right-hand part of peak A contained a 10 kDa band and was included in the pool. The pool was adjusted to 2 M $NH_4SO_4$ and subjected to HIC (FIG. 4B) as described for Equ c 1 in Example 1. Peak J in FIG. 4B was diluted 1:3 in 20 mM Tris, pH 8.0, and applied to a Source™ 15Q column (PE 4.6/100, $V_t$=1.7 mL; GE Healthcare Life Sciences) equilibrated in the same buffer. Elution was performed with a linear gradient of 0-0.4 M NaCl, yielding a dominant peak in the middle of the gradient, followed by a smaller peak (peaks K and L, FIG. 4C). SDS-PAGE analysis was performed using the NuPAGE MES buffer system as described in Example 1 where samples were prepared by diluting the sample 1:3 in NuPAGE LDS buffer with or without 4% β-mercaptoethanol for reducing and non-reducing conditions, respectively. SDS-PAGE analysis of both peaks (FIG. 4D) revealed a band of approximately 15 kDa under non-reducing conditions. Upon reduction of the samples, the 15 kDa band disappeared while two bands of approximately 5 and 10 kDa appeared, suggesting that the unreduced 15 kDa band was made up of the polypeptides forming the 5 kDa and 10 kDa bands, linked to one another by one or more disulfide bridges. Although both peaks appeared to contain the same protein, only the large peak (K) was subjected to further biochemical analysis. For the purpose of IgE binding studies, a refining RPC purification step was included by applying the sample to a Source™ 5 RPC column (ST 2.1/150, $V_t$=0.52 mL; GE Healthcare Life Sciences) equilibrated with 0.065% TFA in water. Elution was performed in a linear 0-70% gradient of buffer B, consisting of 0.05% TFA in 90% acetonitrile. The protein eluted in a single peak near the end of the gradient (Peak M, FIG. 4E).

Identification of the 15 kDa Horse Dander Protein as a Secretoqlobin

The reduced 5 kDa and 10 kDa protein bands, excised and extracted from a SDS-PAGE gel, were analysed by N-terminal sequencing. Analysis of the 5 kDa band revealed the amino acid sequence ATxPAVATDIASFFLLPDSL (x: unresolved residue) (SEQ ID NO: 12), matching residues 22-41 of the predicted *Equus caballus* sequence denoted "similar to LppAB" (Genbank Acc no XP_001502544) (SEQ ID NO: 1). Analysis of the 10 kDa band revealed the sequence GSGx-QLLEDVVEKTITAELS (x: unresolved residue) (SEQ ID NO: 13), matching residues 19-38 of a predicted sequence denoted "similar to Lipophilin CL2" from *Equus caballus* (GenBank Acc no XP_001494564) (SEQ ID NO: 2).

Peptide mass fingerprinting (PMF) analysis of the purified 15 kDa protein by MALDI-TOF MS of an in-solution trypsin digest did not result in any significant match (p<0.05) to known database entries. However, MS-MS analysis of peptides m/z=2281 and m/z=1262.5 identified the sequence QCI-NEISAGDRYIITETLGK (SEQ ID NO: 3) from the predicted sequence "similar to LppAB (*Equus caballus*) (GenBank Acc no XP_001502544.

Peptide mass fingerprinting (PMF) analysis by MALDI-TOF MS of in-gel trypsin digested 5 kDa fragment did not result in any significant match (p<0.05) to known database entries. However, the five dominant peptides detected did all correspond to anticipated trypsin fragments from the SEQ ID NO: 4 where m/z=903.47 (corresponding to residue 28-35), m/z=1037.6 (residues 43-53), m/z=1262.6 (residue 43-53), m/z=2281.1 (residues 43-62) and m/z=2384.2 (residues 1-22), which in total cover 50 (72%) out of the predicted amino acid residues of SEQ ID NO: 4.

Peptide mass fingerprinting (PMF) analysis by MALDI-TOF MS of in-gel trypsin digested 10 kDa band did not result in any significant match (p<0.05) to known database entries. However, the two dominant peptides detected were m/z=1433.6 and m/z=2880.4 which is consistent with the mass of the peptides GSGCQLLEDVVEK and TITAEL-SPAEYVEAVQEFIPDEATEK, respectively, corresponding to residues 1-13 and 14-39 of SEQ ID NO: 5.

The amino acid sequences of both of the identified database entries, XP_001502544 (SEQ ID NO: 6) AND XP_001494564 (SEQ ID NO: 7), contained features characteristic of the secretoglobin protein family. Thus, taken together, the results identified the 15 kDa horse dander protein as a secretoglobin. This protein is hereinafter referred to as Equ c 15k. The predicted full length sequences precursor sequences of the two chains of Equ c 15k are shown in FIG. 5 (5 kDa fragment-SEQ ID NO: 6; 10 kDa fragment-SEQ ID NO 7) where the amino acids identified by N-terminal sequencing are underlined and those identified by MS-MS analysis are shown in bold. The precursor sequence for the 5 kDa fragment includes an N-terminal signal peptide of 21 amino acids, and the precursor sequence for the 10 kDa fragment includes an N-terminal signal peptide of 18 amino acids. It is to be noted that signal peptide prediction of the precursor sequence using SignalP (www.cbs.dtu.dk/services/SignalP) results in the same mature sequences as those obtained experimentally for both the 5 kDa and 10 kDa chains.

Figure 4D:
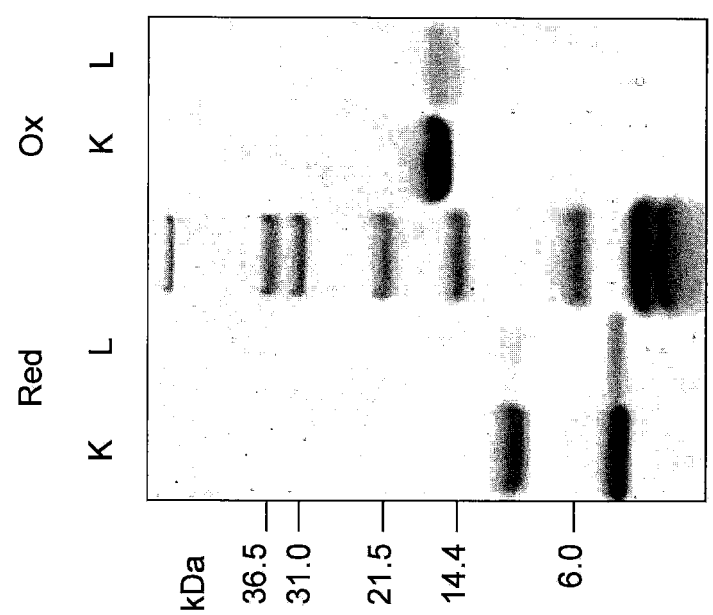
Figure 4E:
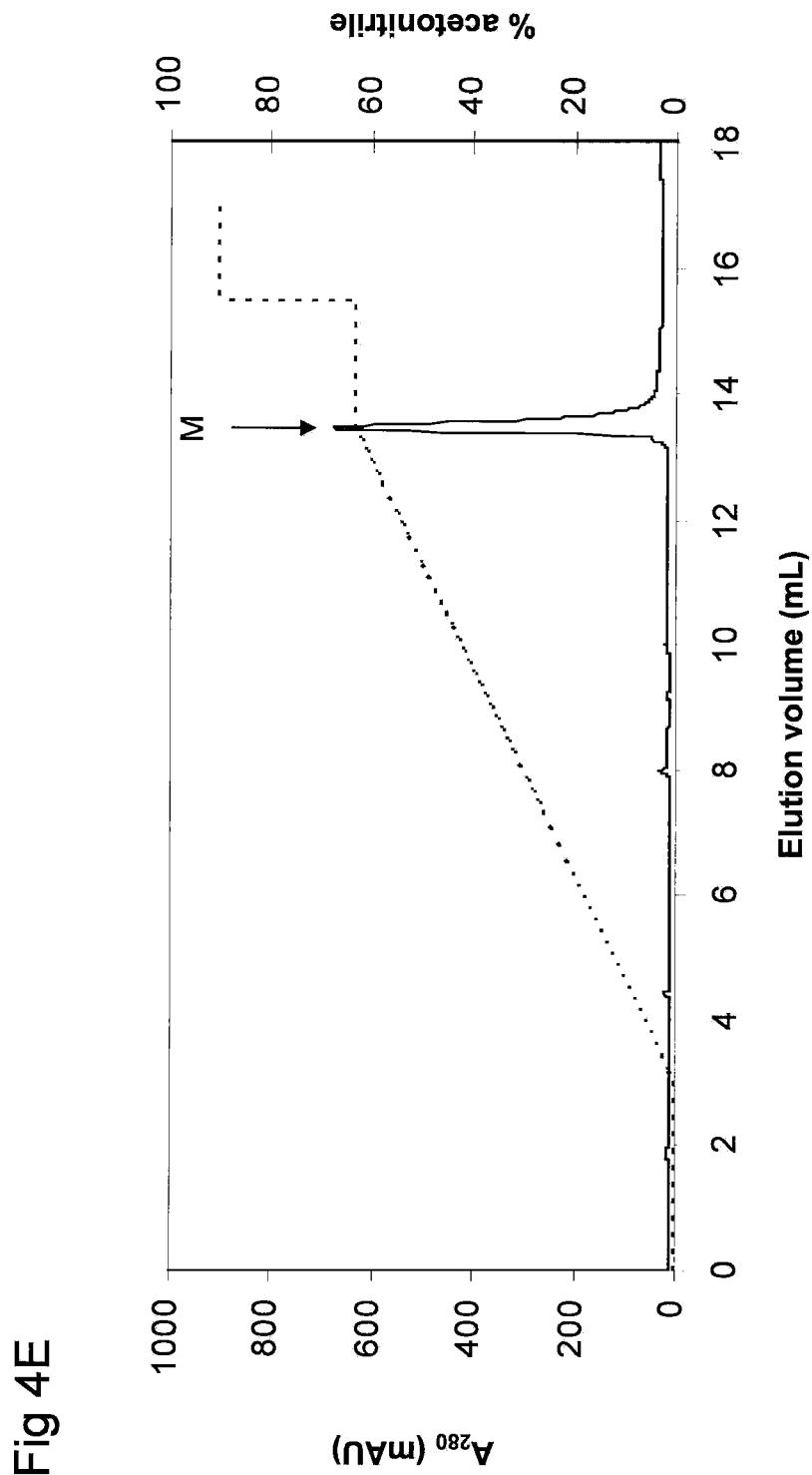

The SDS-PAGE analysis in FIG. 4D provides evidence that the 5 and 10 kDa amino acid chains are held together by one or more disulfide bridges under non-reducing conditions, thereby forming a heterodimeric protein. Thus, the analysis links together a gene encoding a the sequence SEQ ID No 4 with a different gene encoding SEQ ID No 5 that together make up a previously unknown heterodimeric secretoglobin protein.

Example 5

Assessment of IgE Binding to Equ c 15k Using Immunoblot Analysis

With the aim of determining to which subunit of Equ c 15k the IgE reactivity against the protein was directed, an immunoblot analysis was performed employing both reducing and non-reducing conditions.

Immunoblot analysis was performed on reduced and non-reduced samples of purified Equ c 15k separated by SDS-PAGE using a 4-20% NuPAGE gel (Invitrogen) and electroblotted onto a Hybond ECL nitrocellulose membrane (GE Healthcare Life Sciences). Protein blots were blocked for 1 h at room temperature using blocking buffer (50 mM phosphate pH 7.4, 0.1% (v/v) Tween™ 20, 0.9% (w/v) NaCl, 0.3% (w/v) Dextran T10) and then incubated overnight with serum from patient 3 and 12, diluted 1:4.8 and 1:13.5, respectively, in blocking buffer. After washing with 0.15 M NaCl containing 0.5% (v/v) Tween-20, the membrane was incubated 3 hours with a HRP-labelled anti-human IgE antibody in blocking buffer and, after washing, bound IgE was fluorometrically detected using an ECL Advance Western Blotting Detection Kit (GE Healthcare Life Sciences) and a LAS 4000 mini CCD camera (Fujifilm, Tokyo, Japan).

Figure 6:
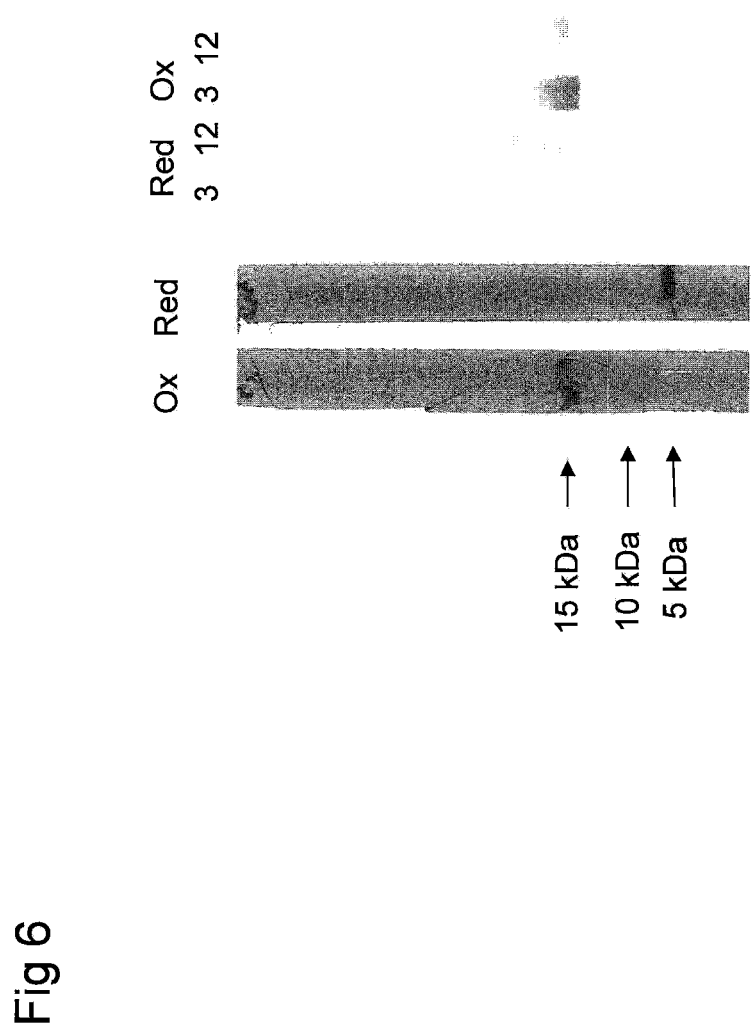
FIG. 6 shows the IgE reactivity to nEqu c 15k in sera of two of the horse allergic patients (Nos. 3 and 12), as detected by immunoblotting. The first two strips show total protein stain and positions of the 5 and 10 kDa subunits and the 15 kDa protein, respectively, are indicated by arrows. The four strips to the right shows the IgE binding to reduced (Red) and non-reduced (Ox) samples of Equ c 15k.

The two sera used in the analysis (patients No. 3 and 12) both had a dominant reactivity to Equ c 15k according to the ImmunoCAP™ analysis (see example 7 below). Both sera reacted only weakly with the subunits of Equ c 15k, dissociated under reducing conditions, visible as faint bands corresponding to the reduced 5 kDa and 10 kDa subunits (FIG. 6). Under non-reducing conditions, a much stronger reactivity was observed with a band coinciding with the non-reduced 15 kDa band of Equ c 15k. No significant reactivity to other bands was observed in this analysis. This immunoblot analysis demonstrates that the IgE binding reactivity is indeed directed to the major protein bands in the Equ c 15k preparation.

Example 6

Production and Immunological Characterization Recombinant Equ c 15k

Cloning and Purification of Recombinant Equ c 15k

A synthetic Equ c 15k single chain gene was designed by combining nucleotide sequences encoding the amino acid sequences of the 5 kDa and the 10 kDa subunits with a sequence encoding a linker peptide comprising 3x (Gly-Gly-Gly-Gly-Ser). The full-length synthetic gene was cloned into the NdeI and XhoI sites of vector pET23a(+) (Novagen, Madison, Wis., USA), adding a C-terminal hexahistidine tag to enable protein purification by immobilised metal ion affinity chromatography (IMAC).

The amino acid sequence for the whole recombinant protein is shown in SEQ ID NO: 8. The nucleotide sequence was designed for optimal codon usage in *E. coli* (DNA2.0, Menlo Park, Calif., USA). The nucleic acid sequence encoding the whole recombinant protein is shown in SEQ ID NO: 9.

The plasmid DNA construct was transformed into *E. coli* strain BL21-AI (Invitrogen) and the recombinant Equ c 15k single chain protein was produced using a 3-liter bioreactor (Belach Bioteknik, Solna, Sweden).

For purification of recombinant Equ c 15k, harvested cells was resuspended in 20 mM Tris-HCl pH 8.0 and lysed by passing the suspension through an Emulsiflex C5 homogenizor (Avestin, Ottawa, Ontario, Canada) at 10 000-15 000 kPa. After centrifugation of the suspension, the pelleted inclusion bodies were dissolved in 6 M Guanidine-HCl, 20 mM Tris pH 8.0, 0.5 M NaCl, 5 mM imidazol and filtered through 0.45 μm mixed cellulose filters (Millipore). The filtered supernatant was applied to a Chelating Sepharose FF column (GE Healthcare Life Sciences), charged with $NiSO_4$. Column washing was performed with 6 M urea in 20 mM Tris-HCl pH 8.0, 0.15 M NaCl, 20 mM imidazole followed by renaturation in situ by a linear 6 M to 2 M gradient of urea in the same buffer. Following renaturation, the recombinant protein was eluted in a linear 20-500 mM gradient of imidazole in the same buffer. Further purification of the recombinant protein was performed by AIEC in 20 mM Tris-HCl pH 8.0 using a Q Sepharose™ FF column (GE Healthcare Life Sciences). The protein was eluted using a linear 0-0.5 M NaCl gradient and fractions were pooled according to SDS-PAGE results. The protein concentration of the final preparation was determined from absorbance at 280 nm, using a calculated extinction coefficient of 0.44 per mg/mL Assessment of IgE Binding to Recombinant Equ c 15k Recombinant Equ c 15k was immobilised to experimental ImmunoCAP™ and the IgE reactivity to sera from 36 horse dander sensitized subjects was determined as described (Marknell DeWitt et al. 2002).

Figure 7:
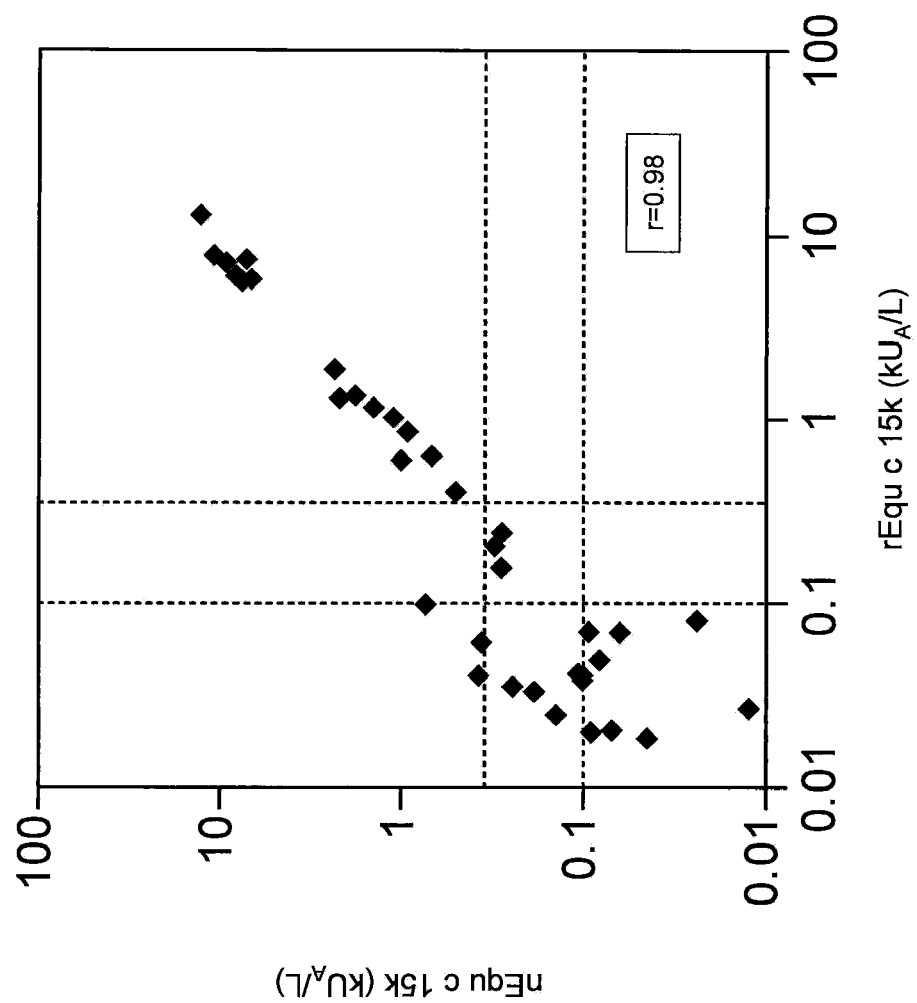
FIG. 7 shows the correlation between the IgE reactivity of native and recombinant Equ c 15k. The 0.35 $kU_A/L$ and 0.1 $kU_A/L$ levels are indicated by dotted lines.

There was a good agreement (r=0.98) between IgE binding to purified native Equ c 15k and recombinant Equ c 15k (FIG. 7), demonstrating that the recombinant protein was immunologically active and structurally similar to the native protein. These data provide strong evidence that the amino acid sequence of the 5 kDa (SEQ ID NO: 4) and 10 kDa (SEQ ID NO: 5) fragments of Equ c 15k, as predicted from the genomic sequence information identified, are correct and represents the amino acid sequence of the purified horse dander allergen Equ c 15k.

Example 7

Assessment of IgE Binding Activity of nEqu c 1, nEqu c 2, nEqu c 3, nEqu c 4/5 and Equ c 15k in a Cohort of Horse Allergic Patients Sera from 25 horse allergic subjects from Spain (n=20) and Sweden (n=5) were used in the study. All patients had a doctors' diagnosis of horse allergy with symptoms such as asthma, rhinoconjunctivitis and urticaria, and a positive skin prick test to horse dander extract. All samples and clinical data were collected under the approval of the local ethics committee at each center contributing to the biobank in which the samples and data had been deposited.

Figure 8:
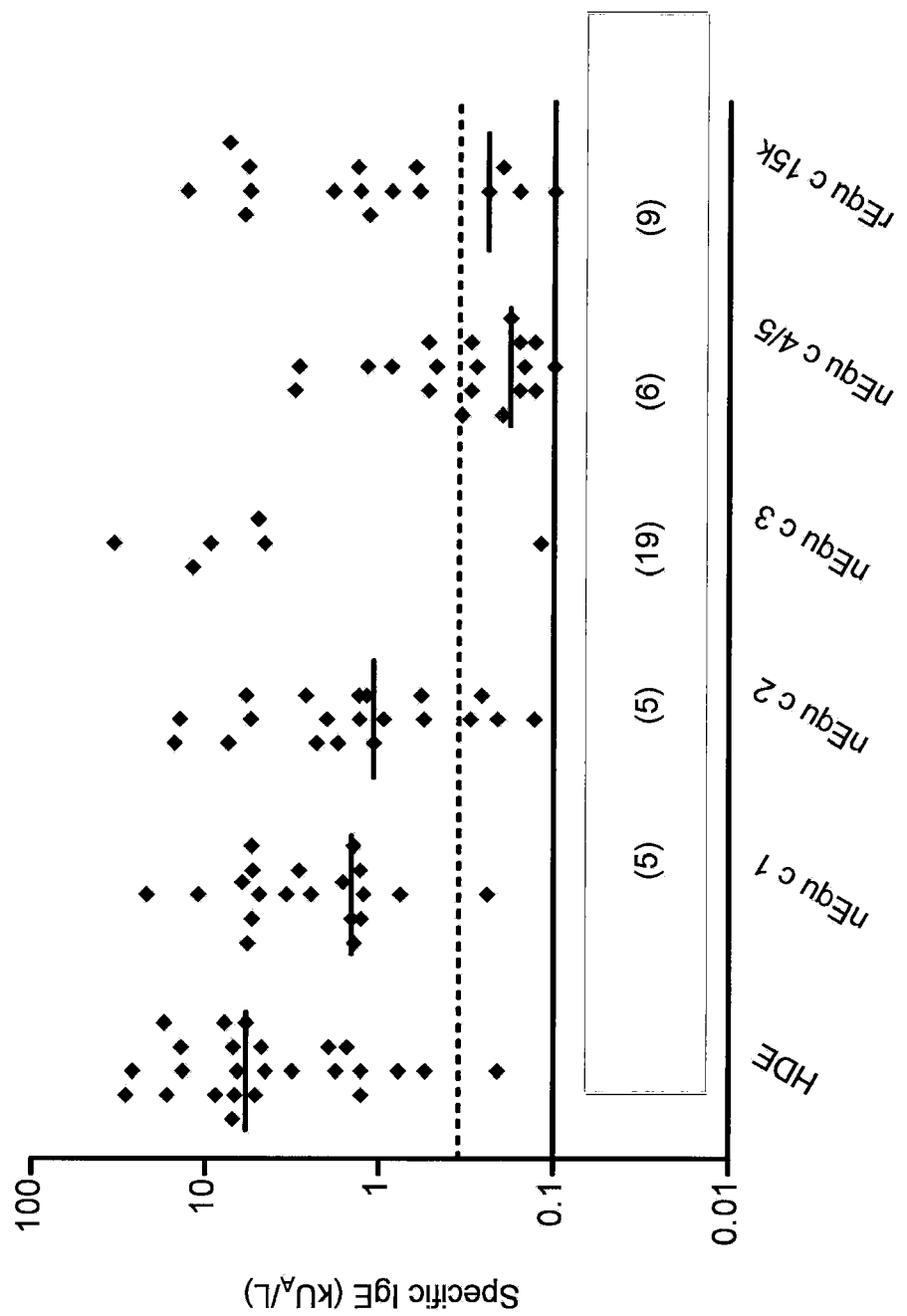
FIG. 8 shows levels of IgE antibodies to horse dander extract (HDE), Equ c 1, nEqu c 2, nEqu c 3. nEqu c 4/5 and rEqu c 15k in a cohort of 25 horse dander allergic subjects. The number of observations below 0.1 $kU_A/L$ is indicated in brackets for each component. Dotted line indicates the 0.35 $kU_A/L$ level and solid line indicates the 0.1 $kU_A/L$ level. Horizontal bars indicate median levels of IgE.

The levels of specific IgE antibodies to horse dander extract, nEqu c 1, nEqu c 2, nEqu c 3 and nEqu c 4/5 and rEqu c 15k among the 25 horse allergic subjects were determined using ImmunoCAP™ (FIG. 8, Table 3). In Table 3, all ImmunoCAP™ levels are displayed as $kU_A/L$ and the origin of each patient is indicated by ES (Spain) or SE (Sweden). Recorded allergic symptoms on exposure to horse are rhinitis (rhin), asthma (astm), urticaria (urt) or anaphylaxis (anaph).

Of the 25 sera tested, 12 (48%) showed an IgE response ≥0.35 $kU_A/L$ to rEqu c 15k, 16 (64%) to nEqu c 2 and 19 (76%) to nEqu c 1. Both nEqu c 3 and nEqu c 4/5 appeared as minor allergens among the subjects studied, binding IgE ab from only 5 (20%) and 7 (28%) of the tested sera, respectively. Four of the 25 sera (16%) reacted exclusively to Equ c 15k. On average among all Equ c 15k-reactive sera, the concentration of IgE antibody to Equ c 15k amounted to 37% of that to horse dander. The corresponding relative concentration of IgE antibody to nEqu c 1 was 52%, whereas for nEqu c 2, nEqu c 3 and nEqu c 4/5 the relative concentrations were 35%, 69% and 9%, respectively, among sera specifically reactive to those allergens. Twenty-four of the 25 sera showed IgE antibody binding to horse dander extract. All of those sera showed binding to at least one of the five individual horse allergens tested. The sum of the IgE binding levels to the individual component matched or exceeded that to horse dander extract.

Example 8

Independent Sensitisation to Equ c 15k and Secretoglobin from Cat, the Major Cat Allergen Fel d 1

Figure 9:
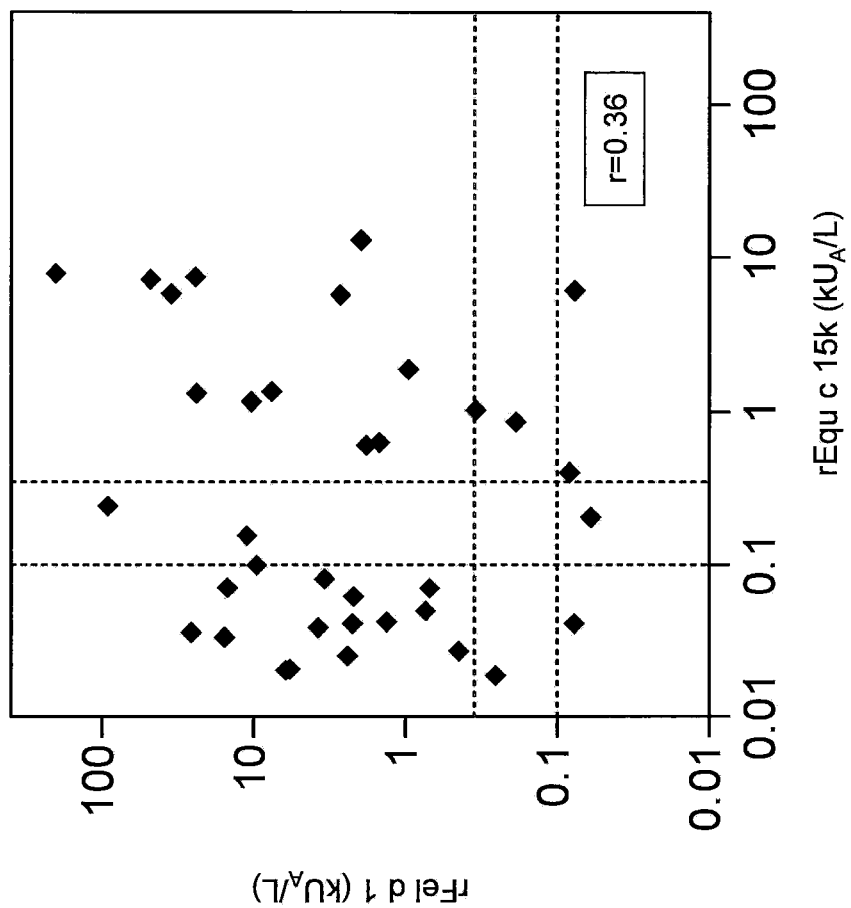
FIG. 9 compares IgE antibody binding to nEqu c 15k and rFel d 1. The 0.35 $kU_A/L$ and 0.1 $kU_A/L$ levels are indicated by dotted lines.

Since Equ c 15k belongs to the secretoglobin protein family, the immunological relationship to the major cat allergen, Fel d 1, which belongs to the same protein family, was investigated. The levels of IgE binding to Fel d 1 was evaluated in sera of 36 horse dander sensitized subjects, including those 25 horse allergic patients described in Example 7. No significant correlation (r=0.36) between the IgE levels to recombinant Equ c 15 and rFel d 1 could be detected (FIG. 9), suggesting that the IgE antibody response to Equ c 15k was predominantly not a result of cross-reactivity between Equ c 15k and Fel d 1, and vice versa.

Figure 10:
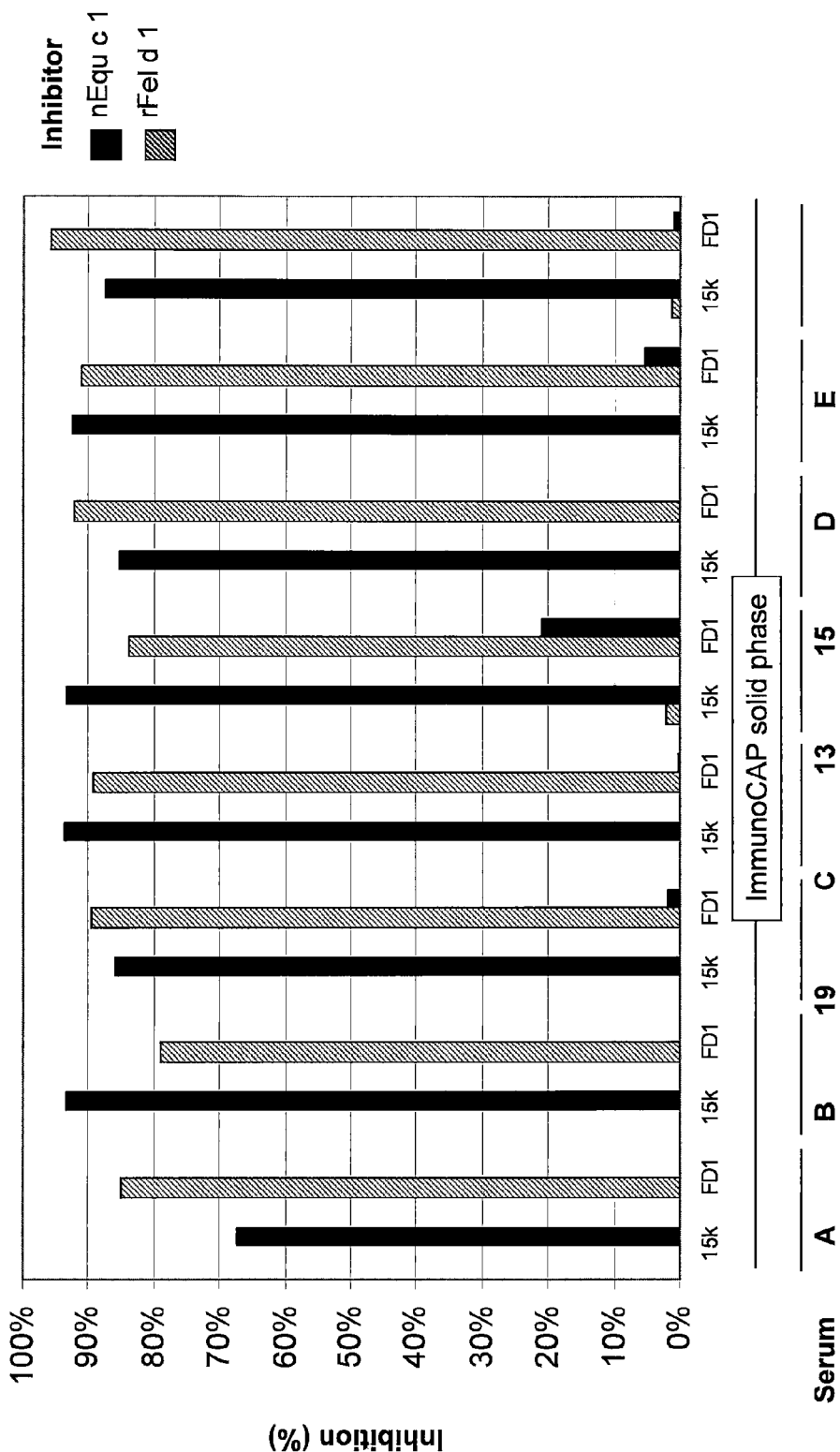
FIG. 10 shows the ability of soluble Equ c 15k and Fel d 1 to self- and cross-inhibit IgE binding to immobilized Equ c 1 and Fel d 1. Sera from horse dander allergic patients (labelled according to table 3) or horse dander sensitised subjects (labelled A to E) were used.

In order to further investigate potential cross reactivity between Equ c 15k and Fel d 1, eight sera displaying significant IgE antibody binding reactivity to both Fel d 1 and Equ c 15k were tested for cross-inhibition, using both rEqu c 15k and rFel d 1 on solid phase as well as nEqu c 15k and rFel d 1 as inhibitors at a final concentration of 100 µg/ml (FIG. 10). As an inhibition control, IgE diluent (Phadia) was used. Means of duplicate determinations of each inhibition were calculated and the fraction of inhibition was calculated as the fraction of the binding using diluent inhibitor that could be quenched with each inhibitor. In these selected sera, inhibition by Fel d 1 could only be achieved when binding to Fel d 1 on the solid phase. Likewise, inhibition using Equ c 15k was only possible on Equ c 15k on the solid phase indicating that in these subjects sensitisation to these to molecules occurred independently of one another and was not a result of cross reactivity. However, the presence of weak cross reactivity between the two proteins cannot be ruled out completely.

TABLE 1

| No | horse dander | nEqu c 1 A | nEqu c 4/5 | nEqu c 2 | Component sum | component coverage (%) |
|---|---|---|---|---|---|---|
| A1 | 44.25 | 4.39 | 0.18 | 0.63 | 5.21 | 12% |
| A2 | 17.08 | 7.96 | 0.83 | 1.40 | 10.20 | 60% |
| A3 | 136.97 | 58.75 | 14.99 | 30.51 | 104.24 | 76% |
| A4 | 11.57 | 1.82 | 0.14 | 0.13 | 2.09 | 18% |
| A5 | 10.43 | 6.47 | 0.20 | 0.54 | 7.21 | 69% |
| A6 | 12.86 | 2.34 | 0.12 | 4.96 | 7.42 | 58% |
| A7 | 9.19 | 5.60 | 1.15 | 1.12 | 7.87 | 86% |
| A8 | 7.26 | 3.37 | 0.17 | 2.07 | 5.60 | 77% |
| A9 | 11.34 | 4.69 | 1.11 | 1.90 | 7.70 | 68% |
| A10 | 33.75 | 3.65 | 0.26 | 20.01 | 23.92 | 71% |
| A11 | 7.39 | 1.09 | 5.34 | 0.85 | 7.28 | 99% |
| A12 | 42.79 | 26.87 | 1.06 | 6.34 | 34.27 | 80% |
| A13 | 0.45 | 0.06 | 0.07 | 0.26 | 0.39 | 87% |
| A14 | 36.70 | 13.32 | 4.25 | 9.41 | 26.98 | 74% |
| A15 | 16.94 | 3.73 | 0.11 | 2.78 | 6.63 | 39% |
| A16 | 1.01 | 3.05 | 0.07 | 0.10 | 3.22 | 319% |
| A17 | 4.97 | 1.36 | 0.42 | 2.03 | 3.81 | 77% |
| A18 | 13.40 | 6.10 | 0.15 | 0.91 | 7.16 | 53% |
| A19 | 7.14 | 2.36 | 0.08 | 0.10 | 2.54 | 36% |
| A20 | 5.20 | 0.24 | 0.50 | 0.20 | 0.94 | 18% |
| A21 | 32.75 | 16.16 | 0.24 | 0.87 | 17.27 | 53% |
| A22 | 13.46 | 3.49 | 0.15 | 0.74 | 4.38 | 33% |
| A23 | 15.28 | 5.09 | 0.16 | 4.30 | 9.55 | 62% |
| A24 | 198.77 | 130.15 | 94.19 | 87.00 | 311.33 | 157% |
| A25 | 42.70 | 11.66 | 7.05 | 13.30 | 32.01 | 75% |
| A26 | 6.55 | 3.23 | 0.36 | 1.77 | 5.36 | 82% |
| A27 | 27.61 | 8.55 | 0.24 | 5.86 | 14.65 | 53% |
| A28 | 8.43 | 4.85 | 0.14 | 0.13 | 5.11 | 61% |
| A29 | 27.12 | 12.81 | 0.67 | 3.29 | 16.77 | 62% |

TABLE 2

| No | Fraction A | Fraction B | Fraction C | Horse dander | Component sum |
|---|---|---|---|---|---|
| A1 | 0.16 | 3.54 | 17.82 | 44.25 | 5.21 |
| A4 | 0.10 | 1.28 | 1.09 | 11.57 | 2.09 |
| A6 | 0.00 | 4.94 | 6.80 | 12.86 | 7.42 |
| A15 | 0.25 | 2.64 | 3.73 | 16.94 | 6.63 |
| A18 | 0.06 | 4.01 | 6.06 | 13.40 | 7.16 |
| A19 | 0.05 | 1.08 | 1.97 | 7.14 | 2.54 |
| A20 | 0.00 | 1.93 | 1.67 | 5.20 | 0.94 |
| A21 | 0.09 | 21.23 | 25.99 | 32.75 | 17.27 |
| A22 | 0.05 | 8.45 | 11.75 | 13.46 | 4.38 |
| A27 | 0.50 | 14.11 | 15.39 | 27.61 | 14.65 |

TABLE 3

| Patient no | symptoms | Country | e3 | nEqu c 1 | nEqu c 2 | nEqu c 3 | nEqu c 4/5 | rEqu c 15k |
|---|---|---|---|---|---|---|---|---|
| 1 | Rhin | SE | 1.55 | 0.06 | 0.21 | 0.12 | 0.30 | 1.31 |
| 2 | Rhin, astm | SE | 1.28 | 1.24 | 0.56 | 0.00 | 0.16 | 0.03 |
| 3 | Rhin | ES | 4.79 | 1.42 | 0.13 | 0.00 | 0.04 | 1.89 |
| 4 | Rhin, astm | ES | 5.87 | 4.96 | 2.32 | 0.07 | 0.53 | 0.16 |
| 5 | Rhin, astm | ES | 1.79 | 1.28 | 0.26 | 0.01 | 0.15 | 0.04 |
| 6 | Rhin, astm | ES | 8.74 | 5.41 | 5.56 | 0.00 | 0.34 | 0.02 |
| 7 | Rhin, astm | ES | 0.21 | 0.00 | 0.02 | 0.00 | 0.02 | 0.20 |
| 8 | Rhin, astm | ES | 4.55 | 1.41 | 2.02 | 0.00 | 0.53 | 0.86 |
| 9 | Rhin | ES | 0.55 | 0.00 | 0.01 | 0.00 | 0.02 | 0.63 |
| 10 | Rhin, astm, urt, anaph | ES | 17.31 | 6.20 | 2.67 | 11.90 | 3.11 | 6.07 |
| 11 | Rhin | ES | 16.62 | 1.30 | 15.15 | 5.04 | 0.86 | 0.10 |
| 12 | Rhin, urt | ES | 13.49 | 2.91 | 1.19 | 0.03 | 0.30 | 12.96 |
| 13 | Rhin, astm, urt | SE | 26.19 | 11.04 | 7.48 | 0.05 | 2.94 | 5.68 |
| 14 | Rhin | SE | 6.58 | 3.42 | 1.08 | 0.01 | 0.48 | 1.16 |
| 15 | Rhin, astm | SE | 7.01 | 0.03 | 0.04 | 0.04 | 0.20 | 7.45 |
| 16 | Rhin | ES | 6.78 | 5.77 | 0.95 | 9.43 | 0.28 | 0.02 |
| 17 | Rhin | ES | 28.73 | 21.92 | 5.89 | 33.75 | 1.19 | 0.24 |
| 18 | Rhin, urt | ES | 13.81 | 5.44 | 14.10 | 0.05 | 0.13 | 0.07 |
| 19 | Rhin, astm | ES | 5.18 | 0.06 | 0.08 | 0.06 | 0.18 | 5.81 |
| 20 | Rhin, astm | ES | 0.78 | 0.76 | 0.09 | 0.01 | 0.02 | 0.02 |
| 21 | Rhin, astm | ES | 1.96 | 1.63 | 0.58 | 0.01 | 0.16 | 0.04 |
| 22 | Rhin, urt | ES | 1.28 | 0.24 | 1.75 | 0.01 | 0.02 | 0.06 |
| 23 | Rhin, astm | ES | 6.94 | 2.49 | 0.30 | 0.00 | 0.10 | 1.36 |
| 24 | Rhin, astm | ES | 3.18 | 1.46 | 1.31 | 0.00 | 0.13 | 0.60 |
| 25 | Rhin | ES | 7.78 | 5.46 | 1.32 | 4.61 | 0.08 | 0.03 |

REFERENCES

Akdis, C. A. (2006). "Allergy and hypersensitivity: mechanisms of allergic disease." Curr Opin Immunol 18(6): 718-726.

Akdis, M. and C. A. Akdis (2007). "Mechanisms of allergen-specific immunotherapy." J Allergy Clin Immunol 119(4): 780-791.

Breiteneder, H., K. Hoffmann-Sommergruber, et al. (1997). "Recombinant allergens; basic and practical considerations." Arbeiten aus dem Paul Ehrlich Institut-Bundesamt fur Sera and Impfstoffe-Zu Frankfurt Am (91): 80-86.

Cabañas, R., M. C. López-Serrano, et al. (2000). "Importance of albumin in cross-reactivity among cat, dog and horse allergens." Journal of Investigational Allergology and Clinical Immunology 10(2): 71-77.

Cromwell, O., H. Fiebig, et al. (2006). "Strategies for recombinant allergen vaccines and fruitful results from first clinical studies." Immunol Allergy Clin North Am 26(2): 261-281, vii.

Dandeu, J. P., J. Rabillon, et al. (1993). "Hydrophobic Interaction Chromatography for Isolation and Purification of Equ.C1, the Horse Major Allergen." Journal of Chromatography-Biomedical Applications 621(1): 23-31.

Demoly, P., B. Lebel, et al. (2003). "Allergen-induced mediator release tests." Allergy 58(7): 553-558.

Ebo, D. G., M. M. Hagendorens, et al. (2004). "In vitro allergy diagnosis: should we follow the flow? [Review]." Clinical & Experimental Allergy 34(3): 332-339.

Goubran Botros, H., C. Gregoire, et al. (1996). "Cross-antigenicity of horse serum albumin with dog and cat albumins: study of three short peptides with significant inhibitory activity towards specific human IgE and IgG antibodies." Immunology 88(3): 340-347.

Goubran Botros, H., P. Poncet, et al. (2001). "Biochemical characterization and surfactant properties of horse allergens." Eur J Biochem 268(10): 3126-3136.

Goubran Botros, H., J. Rabillon, et al. (1998). "Thiophilic adsorption chromatography: purification of Equ c2 and Equ c3, two horse allergens from horse sweat." Journal of Chromatography. B, Biomedical Sciences & Applications 710(1-2): 57-65.

Gregoire, C., I. Rosinski-Chupin, et al. (1996). "cDNA cloning and sequencing reveal the major horse allergen Equ c1 to be a glycoprotein member of the lipocalin superfamily." Journal of Biological Chemistry 271(51): 32951-32959.

Gronlund, H., T. Saarne, et al. (2009). "The Major Cat Allergen, Fel d 1, in Diagnosis and Therapy." Int Arch Allergy Immunol 151(4): 265-274.

Hiller, R., S. Laffer, et al. (2002). "Microarrayed allergen molecules: diagnostic gatekeepers for allergy treatment." FASEB Journal 16(3): 414-416.

Jutel, M., L. Jaeger, et al. (2005). "Allergen-specific immunotherapy with recombinant grass pollen allergens." J Allergy Clin Immunol 116(3): 608-613.

Kim, J. L., L. Elfman, et al. (2005). "Current asthma and respiratory symptoms among pupils in relation to dietary factors and allergens in the school environment." Indoor Air 15(3): 170-182.

Klug, J., H. M. Beier, et al. (2000). "Uteroglobin/Clara cell 10-kDa family of proteins: nomenclature committee report." Ann N Y Acad Sci 923: 348-354.

Liccardi, G., G. D'Amato, et al. (2011). "Sensitization to Horse Allergens in Italy: A Multicentre Study in Urban Atopic Subjects without Occupational Exposure." Int Arch Allergy Immunol 155(4): 412-417.

Marknell DeWitt, Å., V. Niederberger, et al. (2002). "Molecular and immunological characterization of a novel timothy grass (*Phleum pratense*) pollen allergen, Phl p 11." *Clinical & Experimental Allergy* 32(9): 1329-1340.

Mattsson, L., T. Lundgren, et al. (2009). "Prostatic kallikrein: A new major dog allergen." *J Allergy Clin Immunol* 123(2): 362-368.

McDonald, R. E., R. I. Fleming, et al. (2009). "Latherin: a surfactant protein of horse sweat and saliva." *PLoS One* 4(5): e5726.

Ronmark, E., M. Perzanowski, et al. (2003). "Different sensitization profile for asthma, rhinitis, and eczema among 7-8-year-old children: report from the Obstructive Lung Disease in Northern Sweden studies." *Pediatr Allergy Immunol* 14(2): 91-99.

Saarelainen, S., M. Rytkonen-Nissinen, et al. (2008) "Animal-derived lipocalin allergens exhibit immunoglobulin E cross-reactivity." *Clin Exp Allergy* 38(2): 374-381.

Saarne, T., L. Kaiser, et al. (2005). "Rational design of hypoallergens applied to the major cat allergen Fel d 1." *Clin Exp Allergy* 35(5): 657-663.

Smith, W., A. J. Butler, et al. (2004). "Fel d 4, a cat lipocalin allergen." *Clinical & Experimental Allergy* 34(11): 1732-1738.

Spitzauer, S., C. Schweiger, et al. (1993). "Characterisation of dog allergens by means of immunoblotting." *International Archives of Allergy and Immunology* 100: 60-67.

Stumvoll, S., K. Westritschnig, et al. (2003). "Identification of cross-reactive and genuine Parietaria judaica pollen allergens." *Journal of Allergy and Clinical Immunology* 111(5): 974-979.

Tutluoglu, B., S. Atis, et al. (2002). "Sensitization to horse hair, symptoms and lung function in grooms." *Clin Exp Allergy* 32(8): 1170-1173.

Wainstein, B. K., A. Yee, et al. (2007). "Combining skin prick, immediate skin application and specific-IgE testing in the diagnosis of peanut allergy in children." *Pediatr Allergy Immunol* 18(3): 231-239.

Valenta, R., J. Lidholm, et al. (1999). "The recombinant allergen-based concept of component-resolved diagnostics and immunotherapy (CRD and CRIT)." *Clinical and Experimental Allergy* 29(7): 896-904.

Valenta, R. and V. Niederberger (2007). "Recombinant allergens for immunotherapy." *J Allergy Clin Immunol* 119(4): 826-830.

Valenta, R., T. Twaroch, et al. (2007). "Component-resolved diagnosis to optimize allergen-specific immunotherapy in the Mediterranean area." *J Investig Allergol Clin Immunol* 17 Suppl 1: 36-40.

van Eijk, H. M., D. R. Rooyakkers, et al. (1999). "Automated isolation of high-purity plasma albumin for isotope ratio measurements." *Journal of Chromatography. B, Biomedical Sciences and Applications* 731(2): 199-205.

---

The invention claimed is:

1. A diagnostic kit for performing in vitro diagnosis of type 1 allergy, comprising a horse allergen immobilized on a solid support, wherein the horse allergen has a molecular weight of 15 kDa under non-reducing conditions and comprises a first peptide chain having a molecular weight of 5 kDa under reducing conditions and a second peptide chain having a molecular weight of 10 kDa under reducing conditions, the molecular weights measured under denaturing conditions using SDS-PGE, wherein the first peptide segment and the second peptide segment are linked together, and wherein the first peptide segment comprises the amino acid sequence ATCPAVATDIASFFLLPDSLFKLQ-LIKYQAPPEAKDATMQVKQCINEI-SAGDRYIITETLGKIVLQCGA (SEQ ID NO: 4) and the second peptide segment comprises the amino acid sequence GSGCQLLEDVVEKTITAEL-SPAEYVEAVQEFIPDEATEKAAIQLKQ-CYLKQSNETLNDFRTMMNSMYNSAYCALF (SEQ ID NO: 5).

2. The diagnostic kit according to claim 1, wherein the solid support is in a microarray.

3. The diagnostic kit according to claim 1, wherein the solid support is in a lateral flow assay.

4. The diagnostic kit according to claim 1, wherein the solid support is in an immunoassay.

5. The diagnostic kit according to claim 1, wherein the horse allergen comprises the amino acid sequence of SEQ ID NO: 8.

\* \* \* \* \*

UNITED STATES PATENT AND TRADEMARK OFFICE
CERTIFICATE OF CORRECTION

PATENT NO.        : 9,164,101 B2
APPLICATION NO.   : 13/642259
DATED             : October 20, 2015
INVENTOR(S)       : Lars Mattsson et al.

Page 1 of 1

It is certified that error appears in the above-identified patent and that said Letters Patent is hereby corrected as shown below:

IN THE CLAIMS

Claim 1, column 23, line 65, change "SDS-PGE" to --SDS-PAGE--.

Signed and Sealed this
First Day of March, 2016

Michelle K. Lee
*Director of the United States Patent and Trademark Office*

SEQUENCE LISTING

```
<160> NUMBER OF SEQ ID NOS: 13

<210> SEQ ID NO 1
<211> LENGTH: 20
<212> TYPE: PRT
<213> ORGANISM: Equus caballus

<400> SEQUENCE: 1

Ala Thr Cys Pro Ala Val Ala Thr Asp Ile Ala Ser Phe Phe Leu Leu
1               5                   10                  15

Pro Asp Ser Leu
            20

<210> SEQ ID NO 2
<211> LENGTH: 20
<212> TYPE: PRT
<213> ORGANISM: Equus caballus

<400> SEQUENCE: 2

Gly Ser Gly Cys Gln Leu Leu Glu Asp Val Val Glu Lys Thr Ile Thr
1               5                   10                  15

Ala Glu Leu Ser
            20

<210> SEQ ID NO 3
<211> LENGTH: 20
<212> TYPE: PRT
<213> ORGANISM: Equus caballus

<400> SEQUENCE: 3

Gln Cys Ile Asn Glu Ile Ser Ala Gly Asp Arg Tyr Ile Ile Thr Glu
1               5                   10                  15

Thr Leu Gly Lys
            20
```

```
<210> SEQ ID NO 4
<211> LENGTH: 69
<212> TYPE: PRT
<213> ORGANISM: Equus caballus

<400> SEQUENCE: 4

Ala Thr Cys Pro Ala Val Ala Thr Asp Ile Ala Ser Phe Phe Leu Leu
1               5                   10                  15

Pro Asp Ser Leu Phe Lys Leu Gln Leu Ile Lys Tyr Gln Ala Pro Pro
            20                  25                  30

Glu Ala Lys Asp Ala Thr Met Gln Val Lys Gln Cys Ile Asn Glu Ile
        35                  40                  45

Ser Ala Gly Asp Arg Tyr Ile Ile Thr Glu Thr Leu Gly Lys Ile Val
    50                  55                  60

Leu Gln Cys Gly Ala
65

<210> SEQ ID NO 5
<211> LENGTH: 75
<212> TYPE: PRT
<213> ORGANISM: Equus caballus

<400> SEQUENCE: 5

Gly Ser Gly Cys Gln Leu Leu Glu Asp Val Val Glu Lys Thr Ile Thr
1               5                   10                  15

Ala Glu Leu Ser Pro Ala Glu Tyr Val Glu Ala Val Gln Glu Phe Ile
            20                  25                  30

Pro Asp Glu Ala Thr Gly Lys Ala Ala Ile Gln Leu Lys Gln Cys Tyr
        35                  40                  45

Leu Lys Gln Ser Asn Glu Thr Leu Asn Asp Phe Arg Thr Met Met Asn
    50                  55                  60

Ser Met Tyr Asn Ser Ala Tyr Cys Ala Leu Phe
65                  70                  75

<210> SEQ ID NO 6
<211> LENGTH: 90
<212> TYPE: PRT
<213> ORGANISM: Equus caballus

<400> SEQUENCE: 6

Met Arg Leu Phe Leu Pro Val Leu Leu Val Thr Leu Ala Leu Cys Cys
1               5                   10                  15

Cys Glu Thr Asn Ala Ala Thr Cys Pro Ala Val Ala Thr Asp Ile Ala
            20                  25                  30

Ser Phe Phe Leu Leu Pro Asp Ser Leu Phe Lys Leu Gln Leu Ile Lys
        35                  40                  45

Tyr Gln Ala Pro Pro Glu Ala Lys Asp Ala Thr Met Gln Val Lys Gln
    50                  55                  60

Cys Ile Asn Glu Ile Ser Ala Gly Asp Arg Tyr Ile Ile Thr Glu Thr
65                  70                  75                  80

Leu Gly Lys Ile Val Leu Gln Cys Gly Ala
                85                  90

<210> SEQ ID NO 7
<211> LENGTH: 93
<212> TYPE: PRT
<213> ORGANISM: Equus caballus

<400> SEQUENCE: 7
```

```
Met Lys Leu Val Thr Val Leu Met Leu Val Ala Phe Pro Leu Tyr Cys
1               5                   10                  15

Tyr Ala Gly Ser Gly Cys Gln Leu Leu Glu Asp Val Val Glu Lys Thr
            20                  25                  30

Ile Thr Ala Glu Leu Ser Pro Ala Glu Tyr Val Glu Ala Val Gln Glu
        35                  40                  45

Phe Ile Pro Asp Glu Ala Thr Glu Lys Ala Ala Ile Gln Leu Lys Gln
    50                  55                  60

Cys Tyr Leu Lys Gln Ser Asn Glu Thr Leu Asn Asp Phe Arg Thr Met
65                  70                  75                  80

Met Asn Ser Met Tyr Asn Ser Ala Tyr Cys Ala Leu Phe
                85                  90
```

<210> SEQ ID NO 8
<211> LENGTH: 168
<212> TYPE: PRT
<213> ORGANISM: Equus caballus

<400> SEQUENCE: 8

```
Met Ala Thr Cys Pro Ala Val Ala Thr Asp Ile Ala Ser Phe Phe Leu
1               5                   10                  15

Leu Pro Asp Ser Leu Phe Lys Leu Gln Leu Ile Lys Tyr Gln Ala Pro
            20                  25                  30

Pro Glu Ala Lys Asp Ala Thr Met Gln Val Lys Gln Cys Ile Asn Glu
        35                  40                  45

Ile Ser Ala Gly Asp Arg Tyr Ile Ile Thr Glu Thr Leu Gly Lys Ile
    50                  55                  60

Val Leu Gln Cys Gly Ala Gly Gly Gly Ser Gly Gly Gly Gly Ser
65                  70                  75                  80

Gly Gly Gly Gly Ser Gly Ser Gly Cys Gln Leu Leu Glu Asp Val Val
                85                  90                  95

Glu Lys Thr Ile Thr Ala Glu Leu Ser Pro Ala Glu Tyr Val Glu Ala
            100                 105                 110

Val Gln Glu Phe Ile Pro Asp Glu Ala Thr Glu Lys Ala Ala Ile Gln
        115                 120                 125

Leu Lys Gln Cys Tyr Leu Lys Gln Ser Asn Glu Thr Leu Asn Asp Phe
    130                 135                 140

Arg Thr Met Met Asn Ser Met Tyr Asn Ser Ala Tyr Cys Ala Leu Phe
145                 150                 155                 160

Leu Glu His His His His His His
                165
```

<210> SEQ ID NO 9
<211> LENGTH: 504
<212> TYPE: DNA
<213> ORGANISM: Equus caballus

<400> SEQUENCE: 9

```
atggccacgt gccctgcagt cgctacggac atcgcatcgt tcttcttgct gccggacagc      60
ctgtttaagc tgcaactgat caaatatcag gctccgccgg aggccaaaga cgcgaccatg     120
caggttaagc agtgcatcaa cgagattagc gcgggtgatc gctatatcat taccgaaacc     180
ctgggcaaga ttgtgttgca gtgcggtgcc ggtggcggtg gttccggcgg tggcggcagc     240
ggtggtggtg gcagcggtag cggctgtcaa ctgctggaag atgttgtgga gaaaacgatt     300
accgcggagc tgagcccggc tgaatatgtc gaggcggttc aggagtttat tccggacgag     360
```

```
gcaactgaaa aagcagcgat ccaactgaag cagtgttacc tgaaacaaag caacgaaacc      420
ttgaacgatt ttcgtaccat gatgaatagc atgtacaatt ctgcgtactg tgcgctgttc      480
ctcgagcacc accaccacca ccac                                             504

<210> SEQ ID NO 10
<211> LENGTH: 10
<212> TYPE: PRT
<213> ORGANISM: Equus caballus

<400> SEQUENCE: 10

Asp Gln Asp Pro Gln Ser Glu Asp Thr Tyr
1               5                   10

<210> SEQ ID NO 11
<211> LENGTH: 10
<212> TYPE: PRT
<213> ORGANISM: Equus caballus

<400> SEQUENCE: 11

Val Gly Pro Leu Leu Gly Pro Ser Asp Ala
1               5                   10

<210> SEQ ID NO 12
<211> LENGTH: 20
<212> TYPE: PRT
<213> ORGANISM: Equus caballus
<220> FEATURE:
<221> NAME/KEY: MISC_FEATURE
<222> LOCATION: (3)..(3)
<223> OTHER INFORMATION: Unknown

<400> SEQUENCE: 12

Ala Thr Xaa Pro Ala Val Ala Thr Asp Ile Ala Ser Phe Phe Leu Leu
1               5                   10                  15

Pro Asp Ser Leu
            20

<210> SEQ ID NO 13
<211> LENGTH: 20
<212> TYPE: PRT
<213> ORGANISM: Equus caballus
<220> FEATURE:
<221> NAME/KEY: MISC_FEATURE
<222> LOCATION: (4)..(4)
<223> OTHER INFORMATION: Unknown

<400> SEQUENCE: 13

Gly Ser Gly Xaa Gln Leu Leu Glu Asp Val Val Glu Lys Thr Ile Thr
1               5                   10                  15

Ala Glu Leu Ser
            20
```